United States Patent [19]

Kanao

[11] Patent Number: 4,777,257
[45] Date of Patent: * Oct. 11, 1988

[54] CERTAIN TETRAHYDRONAPHTHYL OR INDANYLCARBOXYLATES AND DERIVATIVES THEREOF WHICH INHIBIT THE SYNTHESIS OF THROMBOXANE

[75] Inventor: Munefumi Kanao, Tokyo, Japan

[73] Assignee: Daiichi Seiyaku Co., Ltd., Tokyo, Japan

[*] Notice: The portion of the term of this patent subsequent to May 12, 2004 has been disclaimed.

[21] Appl. No.: 901,694

[22] Filed: Aug. 29, 1986

Related U.S. Application Data

[62] Division of Ser. No. 644,284, Aug. 27, 1984, Pat. No. 4,665,188.

[30] Foreign Application Priority Data

Aug. 25, 1983 [JP] Japan ................. 58-155561
May 21, 1984 [JP] Japan ................. 59-102278
Jun. 1, 1984 [JP] Japan ................. 59-112438
Jun. 12, 1984 [JP] Japan ................. 59-120557
Jul. 5, 1984 [JP] Japan ................. 59-139525
Jul. 16, 1984 [JP] Japan ................. 59-147252

[51] Int. Cl.$^4$ ............... C07D 213/55; C07D 277/32
[52] U.S. Cl. ......................... 546/342; 548/204; 548/341
[58] Field of Search ............... 548/204, 341; 546/342

[56] References Cited
U.S. PATENT DOCUMENTS
4,590,200 5/1986 Cross et al. .................... 514/357

Primary Examiner—Alan L. Rotman
Attorney, Agent, or Firm—Sughrue, Mion, Zinn, Macpeak & Seas

[57] ABSTRACT

Benzocycloalkane derivatives of the formula (I)

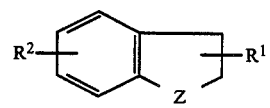

wherein: Z represents a methylene group or an ethylene group, either one of $R^1$ and $R^2$ represents —(CH$_2$)$_m$—COOR$^3$ and the other represents

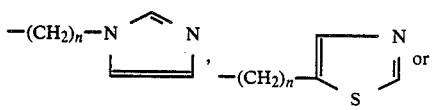

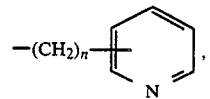

wherein $R^3$ represents a hydrogen atom or an alkyl group having 1 to 6 carbon atoms, n represents an interger of 1 to 6 and m represents an interger of 0 to 5, and the physiologically acceptable salts thereof; having a strong and selective inhibition activity of thromboxane A$_2$ synthesis.

14 Claims, No Drawings

CERTAIN TETRAHYDRONAPHTHYL OR INDANYLCARBOXYLATES AND DERIVATIVES THEREOF WHICH INHIBIT THE SYNTHESIS OF THROMBOXANE

This is a division of application Ser. No. 644,284, filed Aug. 27, 1984, now U.S. Pat. No. 4,665,188.

FIELD OF THE INVENTION

This invention relates to novel benzocycloalkane derivatives which strongly and selectively inhibit the synthesis of thromboxane $A_2$ (hereinafter abbreviated as $TXA_2$) and are useful as therapeutic agents or preventive agents in the treatment of ischaemic heart disease such as myocardial infarction and angina pectoris, thrombosis and cerebral vascular disease such as stroke and infarction.

BACKGROUND OF THE INVENTION $TXA_2$ is a substance derived from arachidonic acid in vivo and has various physiological actions such as vasoconstriction and platelet aggregation. An enhancement of $TXA_2$ synthesis is observed in some patients with angina pectoris. Therefore, it is considered that $TXA_2$ is implicated as a causitive material in ischaemic heart disease.

More particularly, arachidonic acid is transformed to prostaglandin $G_2$ and prostaglandin $H_2$ by cyclooxygenase. Prostaglandin $G_2$ and prostaglandin $H_2$ are transformed to prostacyclin (hereinafter abbreviated as $PGI_2$), prostaglandin $E_2$ (hereinafter abbreviated as $PGE_2$), prostaglandin $F_{2\alpha}$ (hereinafter abbreviated as $PGF_{2\alpha}$), $TXA_2$ and the like by various enzymes in various tissues and organs.

As compounds inhibiting the synthesis of $TXA_2$, a cyclooxygenase inhibitor such as acetylsalicyclic acid and indomethacine, and a $TXA_2$ synthetase inhibitor are reported. The cyclooxygenase inhibitor suppresses not only the synthesis of $TXA_2$ but the synthesis of other prostaglandins such as $PGI_2$, $PGE_2$ and the like. $PGI_2$ has opposite physiological actions to those of $TXA_2$, for example, a powerful vasodilation and inhibition of platelet aggregation. Accordingly, for the above diseases the inhibition of $PGI_2$ synthesis is not preferred.

While, the $TXA_2$ synthetase inhibitor suppresses the synthesis of $TXA_2$ but enhances the synthesis of $PGI_2$. Therefore, the use of the $TXA_2$ synthetase inhibitor is preferred for the above diseases.

Recently, some compounds having the $TXA_2$ synthetase inhibition activity have been proposed as disclosed in Japanese Patent Application (OPI) Nos. 52272/83 and 27874/84 (the term "OPI" as used herein refers to a "published unexamined Japanese Patent Application). The former describes 2-(1-imidazolylmethyl)naphthalene-6-carboxylic acid and 1-methyl-2-(3-pyridylmethyl)naphthalene-7-carboxylic acid and the latter describes 1,2,3,4-tetrahydro-2-(1-imidazolyl)naphthalene-7-carboxylic acid. However, these known compounds do not exhibit a sufficient selective inhibition of $TXA_2$ synthesis.

SUMMARY OF THE INVENTION

This invention relates to a compound of the formula (I)

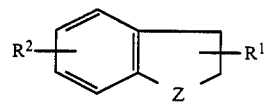

wherein: z represents a methylene group or an ethylene group, either one of $R^1$ and $R^2$ represents $-(CH_2)_m-COOR^3$ and the other represents

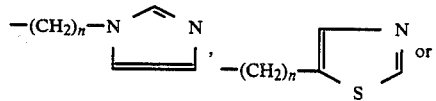

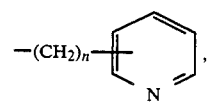

wherein $R^3$ represents a hydrogen atom or an alkyl group having from 1 to 6 carbon atoms, n represents an integer of 1 to 6 and m represents an integer of 0 to 5, and the physiologically acceptable salt thereof.

The compound of this invention can form an acid addition salt with an inorganic acid such as hydrochloric acid and sulfuric acid or an organic acid such as tartaric acid, maleic acid, fumaric acid, methanesulfonic acid and p-toluenesulfonic acid. Moreover, when $R^3$ represents a hydrogen atom the compound of this invention can form a corresponding carboxylate with an alkali metal such as sodium and potassium or an alkaline earth metal such as calcium and magnesium.

The compound of this invention strongly and selectively inhibits the synthesis of $TXA_2$ without inhibiting synthesis of $PGI_2$.

DETAILED DESCRIPTION OF THE INVENTION

This invention relates to novel benzocycloalkane derivatives having the above formula (I).

Referring to m and n in the formula (I), m is preferably 0 and 1 and n is preferably 1 and 2. $R^1$ and $R^2$ are preferably substituted at 1-, 2-, 5-, 6- or 7- position of 1,2,3,4-tetrahydronaphthalene and 2-, 4- or 5- position of indan. Moreover, referring to the definition of $R^1$ and $R^2$, compounds of the formula (I) wherein $R^1$ is

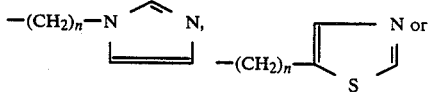

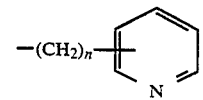

and $R^2$ is $-(CH_2)_m-COOR^3$ are preferred.

Particularly, preferred compounds of this invention are as follows:

(1) 6-(1-imidazolylmethyl)-5,6,7,8-tetrahydro-2-naphthalenecarboxylic acid hydrochloride (2) sodium 6-(5-thiazolymethyl)-5,6,7,8-tetrahydro-2-naphthalenecarboxylate (3) 6-(3-pyridylmethyl)-5,6,7,8-tetrahydro-2-naphthalenecarboxylic acid hydrochloride
(4) sodium 2-(5-thiazolylmethyl)-5-indancarboxylate
(5) sodium 5-(2-(5-thiazolyl)ethyl)-5,6,7,8-tetrahydro-2-naphthalenecarboxylate
(6) 5-(2-(1-imidazolyl)ethyl)-5,6,7,8-tetrahydro-1-naphthalenecarboxylic acid hydrochloride
(7) 2-(1-imidazolylmethyl)-5-indancarboxylic acid hydrochloride.

The compound of the formula (I) includes the compounds illustrated as follows according to the definition of $R^1$ and $R^2$.

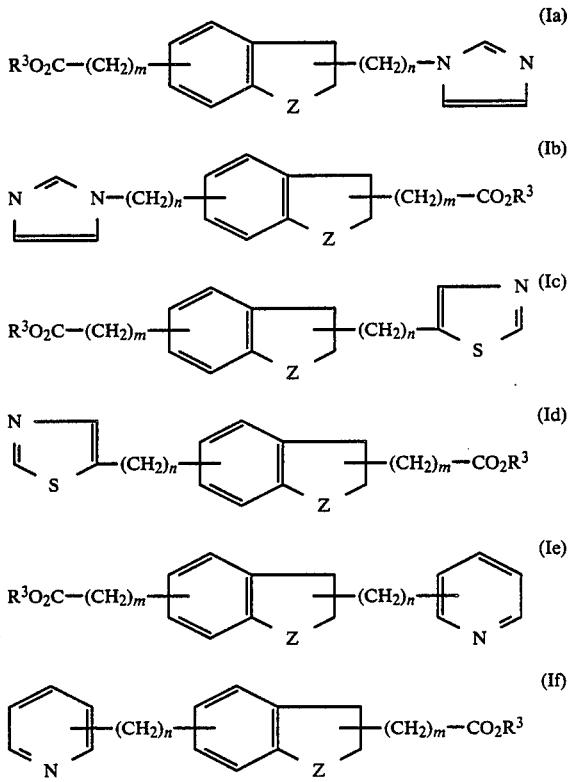

The above compounds can be prepared by the process as described below.

(a) Process for preparing the compound of the formula (Ia)

and benzoyl group, X represents a halogen atom, an alkylsulfonyloxy group such as methanesulfonyloxy group or an arylsulfonyloxy group such as p-toluenesulfonyloxy group and Z, m and n are as defined above.

That is, the compound of the formula (Ia) wherein $R^3$ represents an alkyl group can be prepared by reacting the compound of the formula (II) with imidazole or 1-acylimidazole. The reaction is usually carried out in the presence of a suitable organic solvent such as dimethylformamide, dimethyl sulfoxide, acetonitrile, tetrahydrofuran, N-methylpyrrolidone and the like, at a temperature of from room temperature to a boiling point of the solvent used for 0.5 hour to 3 days. The reaction can be also carried out in the presence of a base such as sodium hydride, sodium alkoxide, potassium tertiary butoxide and the like, or sodium iodide, at a molar ratio of 1 to 2 moles of the base per mole of the compound of formula (II). Imidazole or a 1-acylimidazole is usually employed at a molar ratio of 1 to 1.5 moles per mole of the compound of the formula (II).

In the above reaction, when 1-acylimidazole is employed it is preferred to employ the compound of formula (II) wherein X represents a halogen atom and to carry out the reaction in the presence of sodium iodide in acetonitrile. When imidazole is employed it is preferred to carry out the reaction in the presence of the above base in dimethylformamide at a temperature of from room temperature to 50° C.

The compound thus obtained is then hydrolyzed using a usual hydrolysis reaction with an acid or a base in a suitable solvent to produce the compound of formula (Ia) wherein $R^3$ represents a hydrogen atom. The hydrolysis reaction is usually carried out at a temperature of from room temperature to a boiling point of the solvent used, for 30 minutes to 24 hours. When the acid is employed it is preferred to carry out the reaction at a boiling point of the solvent used. Examples of the base include alkali metal hydroxides such as sodium hydroxide and potassium hydroxide. Examples of the acid include inorganic acids such as hydrochloric acid and sulfuric acid, preferably hydrochloric acid. The acid and base are usually employed in a molar excess to the reactant compound. Examples of the solvent include water and a mixture of water and an alcohol such as methanol and ethanol.

Alternatively, the compound of formula (Ia) can be prepared by the following process:

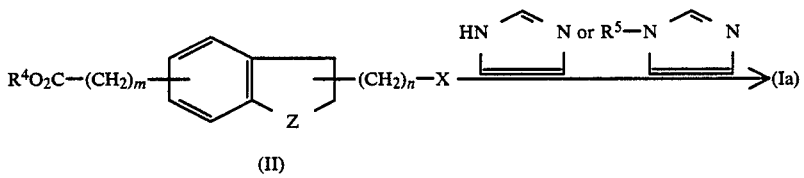

In the above reaction formula, $R^4$ represents an alkyl group having from 1 to 6 carbon atoms, $R^5$ represents an acyl group such as acetyl group, propionyl group

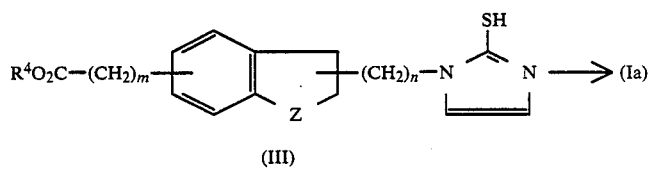

wherein $R^4$, m, n and Z are as defined above.

That is, the compound of formula (III) is reacted with nitric acid and sodium nitrite in acetic acid to produce the compound of the formula (Ia) wherein $R^3$ represents an alkyl group. The ester product is hydrolyzed using the procedure as described for the above reaction to produce the compound of the formula (Ia) wherein $R^3$ represents a hydrogen atom.

(b) Process for preparing the compound of the formula (Ib)

ture thereof, preferably in a mixture of nitric acid and phosphoric acid, and then treating the resulting product with a cuprous halide such as cuprous chloride in hydrohalogenic acid such as hydrochloric acid and hydrobromic acid, preferably in a hydrohalogenic acid corresponding to the halogen atom of the cuprous halide used, and then treating the resulting product with a metal in an organic acid using the procedure as described for the above reaction (2).

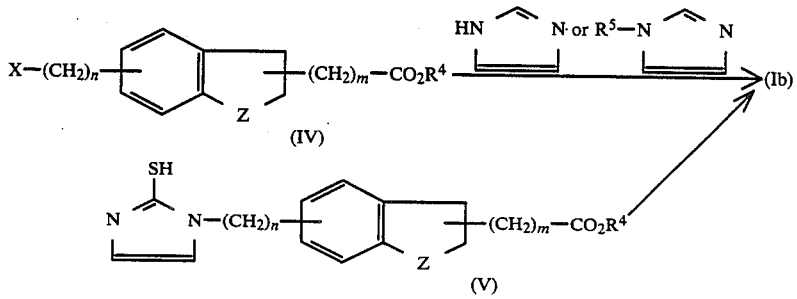

In the above reaction formula, Z, $R^4$, $R^5$, n and m are as defined above.

Using the procedures as described for the process (a), the objective compound of the formula (Ib) can be produced from the compound of the formula (IV) or (V).

(c) Process for preparing the compound of the formula (Ic)

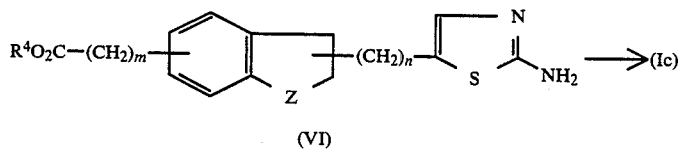

In the above reaction formula, Z, $R^4$, n amd m are as defined above.

That is, the compound of the formula (Ic) wherein $R^3$ represents an alkyl group can be prepared by eliminating the amino group from the compound of the formula (VI). The reaction for eliminating the amino group includes a usual deamination reaction, for example;

(1) a reaction which comprises reacting the amino compound with a lower alkyl nitrite such as tertiary butyl nitrite in a suitable solvent such as dimethylformamide and N-methylpyrrolidone, preferably in dimethylformamide, (2) a reaction which comprises reacting the amino compound with a lower alkyl nitrite such as tertiary butyl nitrite and a cupric halide such as cupric bromide and cupric chloride in a suitable solvent such as acetonitrile, tetrahydrofuran and dioxane, preferably in acetonitrile, and then treating the resulting product with a metal such as zinc, tin and iron, preferably with zinc, in an organic acid such as acetic acid and propionic acid, preferably in acetic acid, and (3) reaction which comprises reacting the amino compound with an alkali metal nitrite such as sodium nitrite in an inorganic acid such as hydrochloric acid, sulfuric acid, nitric acid and phosphoric acid or a mixture thereof, preferably in a mixture of nitric acid and phosphoric acid, and then treating the resulting product with a cuprous halide such as cuprous chloride in hydrohalogenic acid such as hydrochloric acid and hydrobromic acid, preferably in a hydrohalogenic acid corresponding to the halogen atom of the cuprous halide used, and then treating the resulting product with a metal in an organic acid using the procedure as described for the above reaction (2).

The above reaction (1) is usually carried out at a temperature of from 40° C. to a bioling point of the solvent used, preferably at 50° to 70° C., for 30 minutes to 3 hours. The lower alkyl nitrite is usually employed at a molar ratio of 1.1 to 1.5 moles per mole of the amino compound.

In the above reaction (2), the first reaction is usually carried out at a temperature of from room temperature to 80° C., preferably at a temperature near 60° C., until evolution of gas ceases. The second reaction is usually carried out at a temperature of from 40° C. to a bioling point of the solvent used for 1 to 4 hours, preferably 2 to 3 hours. The lower alkyl nitrite is usually employed at a molar ratio of 1.1 to 2 moles per mole of the amino compound and the cupric halide is usually employed at a molar ratio of 1 to 2 moles per mole of the amino compound.

In the above reaction (3), the first reaction is usually carried out at −20° to 15° C., preferably at −10° to 0° C., for 10 minutes to 2 hours. The second reaction is usually carried out at 40° to 60° C. for 30 minutes to 3 hours. The third reaction is usually carried out using the procedure as described for the second reaction of reaction (2). The alkali metal nitrite is usually employed in a slightly molar excess to the amino compound and the cuprous halide is usually employed at a molar ratio of 1 to 2 moles per mole of the product obtained in the first reaction.

The compound thus obtained is hydrolyzed using the procedure as described for the process (a) to produce the compound of formula (Ic) wherein $R^3$ represents a hydrogen atom.

(d) Process for preparing the compoud of the formula (Id)

$$H_2N-\underset{S}{\overset{N}{\diagup\!\!\!\diagdown}}-(CH_2)_n-\!\!\!\left[\!\!\!\begin{array}{c}\phantom{xx}\\Z\end{array}\!\!\!\right]\!\!\!-(CH_2)_m-CO_2R^4 \longrightarrow (Id)$$

(VII)

In the above reaction formula, Z, $R^4$, n and m are as defined above.

Using the procedures as described for the process (c), the objective compound of the formula (Id) can be prepared from the compound of the formula (VII).

(e) Process for preparing the compound of the formula (Ie)

$$R^4O_2C-(CH_2)_m-\!\!\!\left[\!\!\!\begin{array}{c}\phantom{xx}\\Z\end{array}\!\!\!\right]\!\!\!-(CH_2)_n-\!\!\!\left[\!\!\!\begin{array}{c}\phantom{xx}\\N\end{array}\!\!\!\right] \longrightarrow (Ie)$$

(VIII)

In the above reaction formula, $R^4$, Z, n and m are as defined above.

That is, the compound of the formula (Ie) wherein $R^3$ represents a lower alkyl group can be prepared by catalytically reducing the compound of the formula (VIII) in the presence of a catalyst such as palladium carbon, platinic oxide and Raney nickel.

The reaction is usually carried out at a temperature of from room temperature to 50° C. under a pressure of atmospheric pressure to 4 kg/cm² until absorption of hydrogen gas is completed. The catalyst is usually employed at a ratio of not less than 1% by weight to the compound of the formula (VIII).

The compound thus obtained is then hydrolyzed using the procedure as described for the process (a) to produce the compound of the formula (Ie) wherein $R^3$ represents a hydrogen atom.

The starting materials used in the above processes can be prepared by procedures analogous to those of the prior art and the representative processes for preparing these starting materials are described in detail in Referential Examples.

The effect of the compound of the formula (I) on the inhibition of $TXA_2$ synthesis was comfirmed by various tests. The representatives of these tests are described below and the results are shown in Table I.

1. Test of Inhibition of $TXA_2$ Synthesis in Platelet (in vitro)

(i) Preparation of Platelet Rich Plasma (PRP)

Blood was taken by heart puncture from Wistar-Imamichi rats weighing 280–320 g under pentobarbital anesthesia into a syringe containing 0.1 volume of 3.13% sodium citrate, and the citrated blood was centrifuged at 230×g for 7 minutes at room temperature to obtain PRP. The residual blood cell precipitate was further centrifuged at 1,500×g for 10 minutes to obtain platelet poor plasma (PPP). Platelet count of PRP was adjusted to $5\times10^8$/ml by adding PPP.

(ii) Assay of $TXA_2$ and $PGE_2$ Synthesis

90 μl of the PRP was added to 10 μl of test compound solution and mixed by shaking for 1 minute. 90 μl of the mixture was transfered into a tube containing 10 μl of 5 mM sodium arachidonate. The tube was shaken for 5 minutes at room temperature, and then 10 μl of the reaction mixture was poured into a tube containing 90 μl of 100 μM flurbiprofen to stop the reaction.

The reaction mixture was centrifuged at 1,000×g for 5 minutes and the resulting supernatant solution was assayed radioimmuno-chemically for thromboxane $B_2$ (stable degradation product of $TXA_2$, hereinafter abbreviated as $TXB_2$) and $PGE_2$ by the method of Morris et al. (Prostaglandins 21, 771, 1981).

Test compounds and reagents were dissolved in saline or methanol and the solution was diluted with saline to appropriate concentrations before use.

Percent inhibition of $TXA_2$ synthesis was calculated by the formula described below. The inhibitory activity of $TXA_2$ synthesis was expressed in terms of 50% inhibition concentration ($IC_{50}$).

$$\% \text{ Inhibition} = 100 - \frac{\text{test* TXB}_2 \text{ level}}{\text{Control TXB}_2 \text{ level}} \times 100$$

*When test compound was added

It is reported that inhibition of cyclooxygenase results in inhibition of $TXB_2$—, $PGE_2$— and $PGF_2$—synthesis (Hamberg et al. *Proc. Nat. Acad. Sci.* USA, 71, 3824, 1974). In contrast, deficiency or inhibition of $TXA_2$ synthetase is known to increase $PGE_2$—, $PGF_2$— and $PGD_2$—synthesis (Pefreyn et al,. Brit, *J. Haematol*, 49, 29, 1981). Therefore, in order to evaluate the selectivity for inhibition of $TXA_2$ synthetase, a selective index calculated by the following formula was used.

$$\text{Selective Index} = \frac{\text{Test* PGE}_2 \text{ level} - \text{Control PGE}_2 \text{ level}}{\text{Control TXB}_2 \text{ level} - \text{Test* TXB}_2 \text{ level}}$$

*When test compound was added

A high value of the index indicates a relatively high selectivity for inhibition of $TXA_2$ synthetase and a low value indicates a relatively high selectivity for cyclooxygenase inhibition.

2. Test on Inhibition of $TXA_2$ Synthesis and Enhancement of $PGI_2$ Synthesis (ex vivo).

Using the method of Fischer et al. (Circulation, 68, 821 1983), $TXB_2$ and 6-keto-prostaglandin $F_{1\alpha}$ (stable degradation product of $PGI_2$, hereinafter abbreviated as 6-keto-$PGF_{1\alpha}$) levels in serum of incubated whole blood were assayed after single oral administration of 1 mg/kg of test compounds to rats, and the following indications were determined.

$$\% \text{ Inhibition} = 100 - \frac{\text{Test** TXB}_2 \text{ level}}{\text{Control TXB}_2 \text{ level}} \times 100$$

-continued $$\text{Enhancement (fold)} = \frac{\text{Test** 6-keto-PGF}_{1\alpha} \text{ level}}{\text{Control 6-keto-PGF}_{1\alpha} \text{ level}}$$

**When test compound was administered

TABLE I

| Test Compound | Ic$_{50}$ (μM) | Selective*** Index | % Inhibition 1 hr | % Inhibition 3 hr | % Inhibition 6 hr | Enhancement fold (1 hr) |
|---|---|---|---|---|---|---|
| a | 1.1 | 0.81 | 98 | 93 | 88 | 2.91 |
| b | 0.14 | 0.72 | 96 | 88 | 78 | 2.55 |
| c | 0.22 | 0.69 | 97 | 94 | 92 | 2.90 |
| d | 5.4 | 1.10 | 94 | 93 | 76 | 3.02 |
| e | 0.37 | 1.08 | 93 | 93 | 86 | 2.68 |
| f | 6.6 | 0.92 | 95 | 90 | 74 | 3.57 |
| g | 0.40 | 0.98 | 94 | 87 | 52 | 3.52 |
| h | 3.9 | 1.32 | 94 | 84 | 42 | 3.16 |
| i | 3.9 | 0.74 | 96 | | | |
| j | 11 | 0.68 | 50 | 21 | 8 | 1.90 |
| k | 4.5 | 0.60 | 91 | 42 | 11 | 2.50 |
| l | 0.15 | 0.59 | 71 | 64 | 44 | 2.55 |
| m | 3.6 | 0.79 | 93 | 82 | 58 | 2.85 |

***Selective Index when % Inhibition was 80%

Compounds of this invention
a: 6-(1-Imidazolylmethyl)-5,6,7,8-tetrahydro-2-naphthalenecarboxylic acid hydrochloride
b: Sodium 6-(5-thiazolylmethyl)-5,6,7,8-tetrahydro-2-naphthalenecarboxylate
c: 6-(3-Pyridylmethyl)-5,6,7,8-tetrahydro-2-naphthalenecarboxylic acid hydrochloride
d: 5-(2-(1-Imidazolyl)ethyl)-5,6,7,8-tetrahydro-1-naphthalenecarboxylic acid hydrochloride
e: Sodium 5-(2-(5-thiazolyl)ethyl)-5,6,7,8-tetrahydro-1-naphthalenecarboxylate
f: 2-(1-Imidazolylmethyl)-5-indancarboxylic acid hydrochloride
g: Sodium 2-(5-thiazolylmethyl)-5-indancarboxylate
h: 2-(6-(1-Imidazolylmethyl)-1,2,3,4-tetrahydro-1-naphthyl)acetic acid hydrochloride
i: Ethyl 6-(1-imidazolylmethyl)-5,6,7,8-tetrahydro-2-naphthalenecarboxylate hydrochloride
Control compounds
j: 4-(2-(1-Imidazolyl)ethoxy)benzoic acid hydrochloride
k: (E)-3-(4-(1-Imidazolylmethyl)phenyl)propenoic acid hydrochloride
l: Sodium (E)-3-(4-(3-pyridylmethyl)phenyl)-2-methylpropenoate
m: 6-(1-Imidazolylmethyl)-2-naphthalenecarboxylic acid hydrochloride As can be seen from Table I, the compound of the formula (I) exhibits a very strong and selective inhibition of TXA$_2$ synthesis and enhancement of PGI$_2$ synthesis without significantly inhibiting cyclooxygenase as compared with the control compounds. Particularly, the compound of the formula (I) is superior to the control compounds in maintaining the above effects. Moreover, the compound of the formula (I) exhibits a superior effect in other biological tests as compared with the control compounds.

The acute toxicity (LD$_{50}$) of typical compounds of the formula (I) is shown in the following Table II.

TABLE II

| Test compound | LD$_{50}$ (g/kg p.o. in mice) |
|---|---|
| a | 2.17 |
| b | 0.55 |
| g | 0.70 |

TABLE II-continued

| Test compound | LD$_{50}$ (g/kg p.o. in mice) |
|---|---|
| c | 0.75 |

The compound of this invention can be administered orally or parenterally.

For the oral administration, the compound may be used at dosage of about 5 to about 600 mg in adult human per day in the form of various pharmaceutical preparations such as tablets, capsules, powder, granule and the like. The preparations can be prepared by the conventional technique known in the art.

An example of the preparation containing the compound a of this invention is described below.

| Tablets | |
|---|---|
| Compound a | 20 mg |
| Lactose | 50 mg |
| Corn Starch | 25.5 mg |
| Hydroxypropyl Cellulose | 4 mg |
| Magnesium Stearate | 0.5 mg |
| Total | 100 mg per one tablet |

The present invention is further illustrated by the following Examples, but the present invention is not limited thereto.

PRODUCTION OF STARTING MATERIAL

Referential Example 1

(1) 24.5 g of ethyl 6-nitro-4-oxo-1,2,3,4-tetrahydro-2-naphthalenecarboxylate was mixed with 450 ml of ethanol and 0.5 g of 10% palladium carbon and then the mixture was catalytically reduced. After 7 liters of hydrogen gas was absorbed, the catalyst was removed by filtration and the filtrate was concentrated in vacuo. The residue was dissolved in 1 liter of acetic acid and 5.2 g of concentrated sulfuric acid was added thereto. 7 g of 10% palladium carbon was added to the mixture and the resulting mixture was catalytically reduced while warming by irradiation with an infrared lamp. After absorption of hydrogen gas was completed, the catalyst was removed by filtration and the filtrate was concentrated in vacuo.

The residue was dissolved in 300 ml of water and the solution was neutralized by addition of sodium bicarbonate. The mixture was extracted with chloroform. The extract was washed with water, dried over sodium sulfate and then concentrated in vacuo. The residue was dissolved in 100 ml of ethanol and the solution was cooled in an ice-bath and then 30 ml of 48% hydrobromic acid was added thereto. The mixture was concentrated to dryness in vacuo. The crystals obtained were recrystallized from a mixture of ethanol and diethyl ether to give 19.3 g of ethyl 6-amino-1,2,3,4-tetrahydro-2-naphthalenecarboxylate hydrobromide as a colorless powder with m.p. 163°–166° C. (decomposition).

(2) 7.5 g of the above product was suspended in a mixture of 50 ml of water and 4 ml of 48% hydrobromic acid. The suspension was cooled in an ice-bath and then solution of 1.73 g of sodium nitrite in 5 ml of water was added dropwise thereto. The resulting mixture was stirred under cooling in an ice-bath for 20 minutes to give a solution of a diazonium salt.

15.6 g of cupric sulfate pentahydrate and 7.5 g of sodium bromide were dissolved in 50 ml of water and then the solution was stirred at 60°–80° C. A solution of 3.38 g of sodium sulfite and 2.23 g of sodium hydroxide in 25 ml of water was added to the solution and then the mixture was stirred at 60°–80° C. for 10 minutes. After cooling in an ice-bath, the precipitate formed was separated by decantation and washed with water. 50 ml of 48% hydrobromic acid was added to the pricipitate. The mixture was cooled in an ice-bath and the above solution of diazonium salt was added dropwise thereto. The resuting mixture was stirred under cooling in an ice-bath for 30 minutes and at room temperature for 30 minutes and then at 60° C. for 30 minutes. The reaction mixture was cooled in an ice-bath and 200 ml of water was added thereto. The mixture was extracted with chloroform. The extract was washed with water, dried over sodium sulfate and then concentrated in vacuo. The residue was purified by silica gel column chromatography with chloroform eluent to give 4.6 g of ethyl 6-bromo-1,2,3,4-tetrahydro-2-naphthalenecarboxylate as a pale yellow oil.

(3) 5.4 g of the above product was dissolved in 20 ml of tetrahydrofuran and then the solution was added dropwise to a mixture of 0.72 g of lithium aluminum hydride and 40 ml of tetrahydrofuran. The resulting mixture was stirred at room temperature for 1 hour. The reaction mixture was cooled in an ice-bath and then 1 ml of water, 1 ml of a 15% aqueous solution of sodium hydroxide and 3 ml of water were added dropwise thereto successively. The insoluble material was removed by filtration and the filtrate was concentrated in vacuo. The residue was extracted with chloroform. The extract was washed with water, dried over sodium sulfate and then concentrated in vacuo to give 4.28 g of 6-bromo-2-(hydroxymethyl)-1,2,3,4-tetrahydronaphthalene as a colorless oil.

(4) 4.28 g of the above product was mixed with 1.6 g of 2,3-dihydropyran and 2 drops of concentrated hydrochloric acid was added thereto. The mixture was stirred at room temperature for 15 hours. The reaction mixture was extracted with diethyl ether. The extract was washed with normal sodium hydroxide and water successively, dried over sodium sulfate and then concentrated in vacuo to give 5.48 g of 6-bromo-2-(tetrahydropyran-2-yloxymethyl)-1,2,3,4-tetrahydronaphthalene as a pale yellow oil.

(5) A mixture of 1 g of magnesium and 10 ml of tetrahydrofuran was heated at 60°–70° C. under nitrogen gas and then a mixture of 2.44 g of the above product, 1.65 g of bromoethane and 20 ml of tetrahydrofuran was added dropwise thereto. The resulting mixture was heated under reflux for 2 hours under nitrogen gas. The reaction mixture was cooled in an ice-bath and 15 g of dry ice was added thereto. 7 ml of water and 7 ml of 6 normal hydrochloric acid were added to the mixture and the resulting mixture was stirred and then concentrated in vacuo. The residue was extracted with ethyl acetate. The extract was washed with water, dried over sodium sulfate and then concentrated in vacuo. The residue was crystallized from petroleum ether to give 1.5 g of 6-(tetrahydropyran-2-yloxymethyl)-5,6,7,8-tetrahydro-2-naphthalenecarboxylic acid as a colorless powder.

(6) 0.9 g of the above product was mixed with 0.5 ml of concentrated sulfuric acid and 60 ml of ethanol and then the mixture was heated under reflux for 18 hours. 40 ml of water was added to the reaction mixture and the resulting mixture was concentrated in vacuo. The residue was extracted with chloroform. The extract was washed with normal sodium hydroxide and water successively, dried over sodium sulfate and then concentrated in vacuo to give 0.73 g of ethyl 6-(hydroxymethyl)-5,6,7,8-tetrahydro-2-naphthalenecarboxylate as a pale yellow oil.

(7) 0.97 g of the above product was dissolved in 15 ml of pyridine and 1.58 g of p-toluenesulfonyl chloride was added thereto under cooling in an ice-bath. The resulting mixture was stirred at room temperature for 6 hours. The reaction mixture was added to 70 ml of an ice-cold water and the mixture was stirred for 20 minutes. The precipitate formed was collected by filtration to give 1.45 g of ethyl 6-(p-toluenesulfonyloxymethyl)-5,6,7,8-tetrahydro-2-naphthalenecarboxylate as a colorless powder with m.p. 76°–78° C.

Referential Example 2

(1) 24.1 g of 6-bromo-2-hydroxymethyl-1,2,3,4-tetrahydronaphthalene was allowed to react using a procedure analogous to that described in process (7) of Referential Example 1 to give 36.5 g of 6-bromo-2-(p-toluenesulfonyloxymethyl)-1,2,3,4-tetrahydronaphthalene with m.p. 87°–89° C. as a colorless powder.

(2) 20.4 g of diethyl malonate was added to an ethanolic solution of sodium ethoxide prepared from 2.1 g of sodium and 100 ml of ethanol and then 36 g of the above product was added thereto. The mixture was stirred at room temperature for 20 hours and heated under reflux for 24 hours. The reaction mixture was concentrated in vacuo and the residue was extracted with chloroform. The extract was washed with water and dried and then concentrated in vacuo to give 44.5 g of a red oily product. The product was mixed with 10 g of sodium hydroxide and 100 ml of water and then the mixture was heated under reflux for 4 hours. After cooling, the reaction mixture was acidified by addition of 50% sulfuric acid. The precipitate formed was collected by filtration to give 18 g of 2-(6-bromo-1,2,3,4-tetrahydronaphthalene-2-ylmethyl)malonic acid as a powder with m.p. 188°–193° C. (decomposition).

(3) 18 g of the above product was heated at 180° C. for 20 minutes and then 250 ml of ethanol and 5 ml of concentrated sulfuric acid were added thereto. The mixture was heated under reflux for 4 hours. The reaction mixture was concentrated in vacuo and an ice-cold water was added to the residue. The mixture was extracted with chloroform. The extract was washed with water, 2 normal sodium hydroxide and water successively, dried and then concentrated in vacuo to give 17.4 g of ethyl 3-(6-bromo-1,2,3,4-tetrahydronaphthalene-2-yl)propionate as an oil.

(4) 17.3 g of the above product was allowed to react using procedures analogous to those described in steps (3), (4), (5) and (6) of Referential Example 1 to give 11.6 g of ethyl 6-(3-hydroxypropyl)-5,6,7,8-tetrahydro-2-naphthalene carboxylate as an oil.

(5) 11.6 g of the above product was dissolved in 20 ml of dichloromethane. The solution was added dropwise to a suspension of 14.3 g of pyridinium chlorochromate and 90 ml of dichloromethane under cooling in an ice-bath. The mixture was stirred at room temperature for 1.5 hours. 100 ml of diethyl ether was added to the reaction mixture. The supernatant was separated, washed with water, dried and then concentrated in vacuo. The residue was purified by silica gel column chromatography with chloroform eluent to give 10.5 g of ethyl 6-(2-formylethyl)-5,6,7,8-tetrahydro-2-naphthalenecarboxylate as a pale yellow oil.

¹H-NMR (CDCl₃) δ: 1.36 (t, 3H, J=7 Hz, —COOCH₂CH₃), 4.32 (q, 2H, J=7 Hz, —COOCH₂CH₃), 7.05 (d, 1H, J=9 Hz, C₄—H of naphthalene), 7.60-7.80 (m, 2H, C₁ and C₃—H of naphthalene), 9.75 (s, 1H, —CHO).

(6) 2 ml of bromine was added dropwise to 6 ml of dioxane. The mixture was stirred for 10 minutes and dissolved in 25 ml of dichloromethane. The solution was added dropwise to a solution of 10.5 g of the above product in 20 ml of dichloromethane at −10° C. to −5° C. under nitrogen gas. The mixture was stirred at −5° C. for 1 hour and then a solution of 3.1 g of sodium carbonate in 13 ml of water was added dropwise thereto. The resulting mixture was extracted with chloroform. The extract was washed with water, dried and then concentrated in vacuo. The residue was dissolved in 180 ml of ethanol and then 3 g of thiourea was added thereto. The mixture was heated under reflux for 10 hours. The reaction mixture was neutralized by addition of a saturated aqueous solution of sodium bicarbonate and concentrated in vacuo. The residue was extracted with chloroform. The extract was washed with water, dried and then concentrated in vacuo. The residue was purified by silica gel column chromatography with chloroform eluent to give 5.73 g of ethyl 6-(2-amino-5-thiazolylmethyl)-5,6,7,8-tetrahydro-2-naphthalenecarboxylate as a colorless powder with m.p. 150°-153° C.

Referential Example 3

(1) 5-bromo-1-(2-hydroxyethyl)-1,2,3,4-tetrahydronaphthalene was allowed to react using procedures analogous to those described in step (7) of Referential Example 1, steps (2) and (3) of Referential Example 2, steps (3), (4), (5) and (6) of Referential Example 1 and steps (5) and (6) of Referential Example 2 to give ethyl 5-(2-(2-amino-5-thiazolyl)ethyl)-5,6,7,8-tetrahydro-1-naphthalenecarboxylate as an oil.

Referential Example 4

(1) Ethyl 6-nitro-1,2,3,4-tetrahydro-4-oxo-2-naphthalenecarboxylate was treated according to the procedure described in step (1) of Referential Example 1 but using concentrated hydrochloric acid instead of 48% hydrobromic acid to give ethyl 6-amino-1,2,3,4-tetrahydro-2-naphthalenecarboxylate hydrochloride with m.p. 117°-130° C. (decomposition).

(2) 11 g of the above product was mixed with 4 ml of concentrated hydrochloric acid and 40 ml of acetone. The mixture was cooled in an ice-bath and then a solution of 3.3 g of sodium nitrite in 4 ml of water was added dropwise thereto at 0°-5° C. After 20 minutes, 25 ml of acrolein and 200 mg of cuprous chloride were added to the mixture. The resulting mixture was stirred at 35°-40° C. for 3 hours. The reaction mixture was concentrated in vacuo and the residue was extracted with benzene. The extract was washed with water, dried and then concentrated in vacuo.

The residue was dissolved in 100 ml of ethanol and 3.64 g of thiourea was added thereto. The resulting mixture was heated under reflux for 16 hours. The reaction mixture was concentrated in vacuo and the residue was neutralized by addition of sodium bicarbonate and then the mixture was extracted with chloroform. The extract was washed with water, dried and then concentrated in vacuo. The residue was purified by silica gel column chromatography using a mixture of ethanol and chloroform (2:98 by volume) for elution to give 6.0 g of ethyl 6-(2-amino-5-thiazolylmethyl)-1,2,3,4-tetrahydro-2-naphthalenecarboxylate as a powder with m.p. 147°-149° C.

Referential Example 5

(1) 15.2 g of ethyl 6-amino-1,2,3,4-tetrahydro-2-naphthalenecarboxylate hydrobromide was dissolved in a mixture of 12 ml of concentrated hydrochloric acid and 10 ml of water. The solution was cooled in an ice-bath and then a solution of 4.46 g of sodium nitrite in 7 ml of water was added dropwise thereto. The resulting mixture was stirred at 0° C. for 30 minutes to give a solution of diazonium salt.

0.2 g of sodium sulfite was dissolved in 36 ml of water and 1.28 g of cupric sulfate pentahydrate was added thereto. The mixture was stirred and then 33.4 g of sodium acetate, and a mixture of 2.33 g of paraform, 5.33 g of hydroxylamine hydrochloride and 35 ml of water were added thereto successively. The resulting mixture was cooled at 10° C. and then a solution prepared from the above diazonium solution and 7 g of sodium acetate was added dropwise thereto. The mixture was stirred for 1 hour and 50 ml of concentrated hydrochloric acid was added thereto. The resulting mixture was heated under reflux for 2 hours. After cooling, the reaction mixture was extracted with ethyl acetate. The extract was washed with water, dried and then concentrated in vacuo. 40 ml of 40% aqueous solution of sodium bisulfite was added to the residue and the mixture was stirred at 60°-80° C. for 3 hours. The reaction mixture was shaken with 100 ml of ethyl acetate and an aqueous layer was separated. 15 ml of concentrated sulfuric acid was added to the aqueous solution. The mixture was stirred at room temperature for 18 hours and heated under reflux for 30 minutes. After cooling, the reaction mixture was extracted with ethyl acetate. The extract was washed with water, dried and then concentrated to dryness in vacuo. The residue was washed with petroleum ether to give 3.46 g of 6-formyl-1,2,3,4-tetrahydro-2-naphthalenecarboxylic acid as a yellow powder with m.p. 205°-212° C.

(2) 4.4 g of the above product was added to a mixture of 150 ml of ethanol and 2 ml of sulfuric acid and then the mixture was heated under reflux for 1 hour. The reaction mixture was concentrated in vacuo. The residue was dissolved in chloroform. The solution was washed with water, dried and then concentrated in vacuo to give 5.0 g of ethyl 6-formyl-1,2,3,4-tetrahydro-2-naphthalenecarboxylate as a yellow oil.

(3) 5.0 g of the above product was dissolved in 100 ml of ethanol, and 0.4 g of sodium borohydride was added portionwise thereto under cooling in an ice-bath. The mixture was stirred for 20 minutes. 2 normal hydrochloric acid was added to the reaction mixture and the resulting mixture was concentrated in vacuo. The residue was extracted with chloroform. The extract was washed with water, dried and then concentrated in vacuo to give 5.03 g of ethyl 6-(hydroxymethyl)-1,2,3,4-tetrahydro-2-naphthalenecarboxylate as a yellow oil.

¹H-NMR (CDCl₃) δ: 1.28 (3H, t, J=7 Hz, —CO₂CH₂CH₃), 1.76 (1H, s, —OH), 1.6-2.4 (2H, m, C₃—H of naphthalene), 2.5-3.1 (5H, m, C₁, C₂ and C₄—H of naphthalene), 4.18 (2H, q, J=7 Hz, —CO₂CH₂CH₃), 4.61 (2H, s, —CH₂OH), 7.09 (3H, m, C₅, C₇ and C₈—H of naphthalene).

(4) 5.03 g of the above product was mixed with 40 ml of thionyl chloride and the mixture was heated under reflux for 1.5 hours. The reaction mixture was concentrated in vacuo to give ethyl 6-(chloromethyl)-1,2,3,4- tetrahydro-2-naphthalenecarboxylate as a crude product.

Referential Example 6

(1) 2.75 g of 50% sodium hydride was suspended in 120 ml of tetrahydrofuran and 14.5 g of triethyl phosphonoacetate was added thereto. The mixture was stirred at room temperature for 15 minutes and 10.2 g of 5-oxo-5,6,7,8-tetrahydro-2-naphthonitrile was added thereto.

The resulting mixture was heated under reflux for 1 hour. After cooling, water was added to the reaction mixture and the mixture was extracted with ethyl acetate. The extract was washed with water and dried and then concentrated in vacuo. The residue was purified by column chromatography on 100 g of silica gel to give an oily product. The product was dissolved in 80 ml of ethanol and 1.5 g of 10% palladium carbon was added thereto. The mixture was catalytically reduced. After absorption of hydrogen gas was completed, the catalyst was removed by filtration. The filtrate was concentrated in vacuo to give 12.1 g of ethyl 2-(6-cyano-1,2,3,4-tetrahydro-1-naphthyl)acetate as crystals with m.p. 45°–47° C.

(2) 10 ml of ethanol and 0.5 ml of Raney nickel catalyst were added to 0.73 g of the above product. The mixture was catalytically reduced. After absorption of hydrogen gas was completed, the catalyst was removed by filtration and the filtrate was concentrated in vacuo. The residue was treated with 2 normal hydrochloric acid and shaken with ethyl acetate. The aqueous layer was separated and adjusted to pH 9–10 with an aqueous solution of sodium hydroxide and then extracted with ethyl acetate. The extract was washed with water, dried and then concentrated in vacuo to give 0.62 g of ethyl 2-(6-(aminomethyl)-1,2,3,4-tetrahydro-1-naphthyl)acetate as an oil.

(3) 0.62 g of the above product was dissolved in a mixture of 5 ml of chloroform and 1 ml of pyridine and then 0.5 ml of acetic anhydride was added thereto. The mixture was allowed to stand for 2 days and 5 ml of water was added thereto. The resulting mixture was stirred for 1 hour and the organic layer was separated. The solution was washed with water, dried and then concentrated in vacuo to give 0.71 g of ethyl 2-(6-(acetaminomethyl)-1,2,3,4-tetrahydro-1-naphthyl)acetate as an oil.

(4) 2.9 g of the above product was dissolved in a mixture of 50 ml of acetic anhydride and 10 ml of acetic acid. 7.5 g of sodium nitrite was added to the solution over a period of 2 hours under cooling in an ice-bath. The mixture was stirred for 1 hour under cooling in an ice-bath and concentrated in vacuo. The residue was treated with normal hydrochloric acid and extracted with chloroform. The extract was washed with water and a saturated aqueous solution of sodium bicarbonate successively, dried and then concentrated in vacuo. The oily residue was added to 200 ml of benzene and the mixture was heated under reflux for 24 hours. After cooling, the reaction mixture was washed with water, dried and then concentrated in vacuo to give 2.3 g of ethyl 2-(6-(acetyloxymethyl)-1,2,3,4-tetrahydro-1-naphthyl)acetate as an oil.

(5) 2.3 g of the above product was added to a mixture of 100 ml of ethanol and 1 ml of concentrated sulfuric acid. The mixture was heated under reflux for 20 hours. The reaction mixture was concentrated in vacuo and the residue was neutralized by addition of sodium bicarbonate and extracted with chloroform. The extract was washed with water, dried and then concentrated in vacuo to give 2.1 g of ethyl 2-(6-(hydroxymethyl)-1,2,3,4-tetrahydro-1-naphthyl)acetate.

(6) 1.8 g of the above product was dissolved in 40 ml of benzene, and 4 ml of thionyl chloride was added thereto. The mixture was heated under reflux for 1 hour. The reaction mixture was concentrated to dryness in vacuo and water was added to the residue. The mixture was neutralized by addition of sodium bicarbonate and extracted with chloroform. The extract was washed with water, dried and then concentrated in vacuo to give 1.8 g of ethyl 2-(6-(chloromethyl)-1,2,3,4-tetrahydro-1-naphthyl)acetate as a colorless oil.

$^1$H-NMR (CDCl$_3$) δ: 1.27 (3H, t, —CO$_2$CH$_2$C$\underline{H}_3$), 1.8 (4H, m, C$_2$ and C$_3$—H of naphthalene), 2.3–2.6 (2H, m, —C$\underline{H}_2$CO$_2$—), 2.74 (2H, m, C$_4$—H of naphthalene), 3.3 (1H, m, C$_1$—H of naphthalene), 4.15 (2H, q, —CO$_2$C$\underline{H}_2$CH$_3$), 4.49 (2H, s, —CH$_2$Cl).

Referential Example 7

(1) 5.0 g of ethyl 5-oxo-5,6,7,8-tetrahydro-2-naphthalenecarboxylate was mixed with 2.5 g of 3-pyridinealdehyde, 10 ml of acetic acid and 10 ml of piperidine and then the mixture was stirred at 100° C. for 4 hours. The reaction mixture was concentrated in vacuo and the residue was dissolved in ethyl acetate. 10% Hydrochloric acid was added to the solution. The aqueous layer was separated and neutralized by addition of sodium bicarbonate. The mixture was extracted with chloroform. The extract was washed with water, dried and then concentrated in vacuo. The residue was purified by silica gel column chromatography to give 5.6 g of ethyl 6-(3-pyridylmethylidene)-5-oxo-5,6,7,8-tetrahydro-2-naphthalenecarboxylate as pale yellow crystals with m.p. 112°–114° C.

(2) 6.3 g of the above product was mixed with 50 ml of ethanol, 50 ml of ethyl acetate and 1 g of 10% palladium carbon. The mixture was catalytically reduced. After absorption of hydrogen gas was completed, the catalyst was removed by filtration. The filtrate was concentrated in vacuo. The residue was purified by silica gel column chromatography to give 4.8 g of ethyl 6-(3-pyridylmethyl)-5-oxo-5,6,7,8-tetrahydro-2-naphthalenecarboxylate as an oil.

(3) 3 g of the above product was dissolved in 50 ml of ethanol, and 0.9 g of sodium borohydride was added portionwise thereto. The mixture was heated under reflux for 1 hour. The reaction mixture was concentrated in vacuo and water was added to the residue. The mixture was extracted with chloroform. The extract was washed with water, dried and then concentrated in vacuo to give an oily product. The product was dissolved in 80 ml of ethanol, and 20 ml of concentrated hydrochloric acid was added thereto. The mixture was heated under reflux for 5 hours. The reaction mixture was neutralized by addition of sodium bicarbonate and the mixture was concentrated in vacuo. The residue was dissolved in chloroform. The chloroform solution was washed with water, dried and then concentrated in vacuo. The residue was purified by silica gel column chromatography to give 1.8 g of ethyl 6-(3-pyridylmethyl)-7,8-dihydro-2-naphthalenecarboxylate as an oil.

$^1$H-NMR (CDCl$_3$) δ: 1.36 (3H, t, —CO$_2$CH$_2$C$\underline{H}_3$), 2.0–2.4 (2H, m, C$_7$—H of naphthalene), 2.6–2.9 (2H, m, C$_8$—H of naphthalene), 3.5 (2H, m,

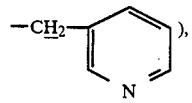

4.32 (2H, q, —CO$_2$CH$_2$CH$_3$), 6.21 (1H, m, C$_5$—H of naphthalene), 6.9–8.45 (7H, m, hydrogen of aromatic ring).

Referential Example 8

(1) 14.8 g of 6-bromo-1-oxo-1,2,3,4-tetrahydronaphthalene was allowed to react using a procedure analogous to that described in step (1) of Referential Example 6 to give 15.5 g of an oily product. The product was constituted of ethyl 2-(6-bromo-1,2,3,4-tetrahydro-1-naphthylidene)acetate as a main product and a small amount of ethyl 2-(6-bromo-3,4-dihydro-1-naphthyl)acetate as a by-product.

(2) 15.5 g of the above product was allowed to react using a procedure analogous to that described in step (3) of Referential Example 1 to give 11.7 g of an oily product. The product was constituted of 6-bromo-1-(2-hydroxyethyl)-1,2,3,4-tetrahydronaphthalene as a main product and a small amount of 6-bromo-1-(2-hydroxyethyl)-3,4-dihydronaphthalene as a by-product.

(3) 11.7 g of the above product was allowed to react using a procedure analogous to that described in step (4) of Referential Example 1 to give 14.3 g of an oily product. The product was constituted of 6-bromo-1-(2-(tetrahydropyran-2-yloxy)ethyl)-1,2,3,4-tetrahydronaphthalene as a main product and a small amount of 6-bromo-1-(2-tetrahydropyran-2-yloxy)ethyl)-3,4-dihydronaphthalene as a by-product.

(4) 14.3 g of the above product was allowed to react using procedures analogous to those described in steps (5) and (6) of Referential Example 1 but using iodomethane instead of bromoethane to give an oily product containing a small amount of ethyl 5-(2-hydroxyethyl)-7,8-dihydro-2-naphthalenecarboxylate as a by-product. The product was dissolved in 10 ml of ethanol and 0.5 g of 10% palladium carbon was added thereto. The mixture was catalytically reduced. After absorption of hydrogen gas was completed, the catalyst was removed by filtration. The filtrate was concentrated in vacuo to give 1.4 g of ethyl 5-(2-hydroxyethyl)-5,6,7,8-tetrahydro-2-naphthalenecarboxylate as an oil.

(5) 1.4 g of the above product was allowed to react using a procedure analogous to that described in step (7) of Referential Example 1 to give 2.1 g of ethyl 5-(2-(p-toluenesulfonyloxy)ethyl)-5,6,7,8-tetrahydro-2-naphthalenecarboxylate as an oil.

$^1$H-NMR (CDCl$_3$) δ: 1.37 (3H, t, —CO$_2$CH$_2$CH$_3$), 2.45 (3H, s,

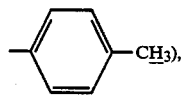

2.9–3.1 (3H, m, C$_5$—H of naphthalene), 4.11 (2H, t, —CH$_2$OSO$_2$—), 4.31 (2H, q, —CO$_2$CH$_2$CH$_3$), 7.28 (2H, d, aromatic hydrogen of tosyl), 6.98 (1H, d, C$_4$—H of naphthalene).

Referential Example 9

5-bromo-1-oxo-1,2,3,4-tetrahydronaphthalene was allowed to react using procedures analogous to those described in Referential Example 8 to give 5-(2-(p-toluenesulfonyloxy)ethyl)-5,6,7,8-tetrahydro-1-naphthalenecarboxylate as an oil.

$^1$H-NMR (CDCl$_3$) δ: 1.36 (3H, t, —CO$_2$CH$_2$CH$_3$), 1.60–2.20 (6H, m, C$_6$ and C$_7$—H of naphthalene and —CH$_2$CH$_2$O—), 2.45 (3H, s,

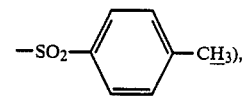

2.60–3.25 (3H, m, C$_5$ and C$_8$—H of naphthalene), 4.13 (2H, t, —CH$_2$OSO$_2$—), 4.32 (2H, q, —CO$_2$CH$_2$CH$_3$), 7.0–7.9 (7H, m, hydrogen of aromatic ring).

Referential Example 10

(1) 7.6 g of ethyl 5-oxo-5,6,7,8-tetrahydro-2-naphthalenecarboxylate was mixed with 6.4 g of ethyl chloroacetate. The mixture was cooled to 5°–10° C. and then a mixture of 5.9 g of potassium tertiary butoxide and 65 ml of tertiary butanol was added thereto over a period of 1 hour. The resulting mixture was stirred at room temperature for 4 hours. The reaction mixture was concentrated in vacuo at a temperature not more than 30° C. The residue was extracted with diethyl ether and the extract was washed with water, dried and then concentrated in vacuo to give an oily product. The product was dissolved in 25 ml of ethanol. A solution of 0.58 g of sodium in 25 ml of ethanol, and 0.43 ml of water were added successively to the solution. The mixture was stirred at room temperature for 4 hours. Diethyl ether was added to the reaction mixture and the precipitate formed was collected by filtration. The precipitate was mixed with 10 ml of acetic acid and the mixture was heated at 100° C. for 15 minutes. After cooling, water was added to the reaction mixture and the mixture was extracted with diethyl ether. The extract was washed with water, dried and then concentrated in vacuo to give 3.6 g of ethyl 5-formyl-5,6,7,8-tetrahydro-2-naphthalenecarboxylate as an oil.

(2) 3.6 g of the above product and 2.2 g of aminoacetal were mixed with 70 ml of benzene. The mixture was heated for 3 hours while removing the water produced. The reaction mixture was concentrated in vacuo and the oily product was dissolved in 30 ml of ethanol. 1.2 g of sodium borohydride was added portionwise to the solution and the mixture was stirred at room temperature for 1 hour. The reaction mixture was concentrated in vacuo and the residue was extracted with diethyl ether. The extract was washed with water, dried and then concentrated in vacuo. The residue was purified by silica gel column chromatography to give 2.5 g of ethyl 5-(N-(2,2-diethoxyethyl)aminomethyl)-5,6,7,8-tetrahydro-2-naphthalenecarboxylate as an oil.

$^1$H-NMR (CDCl$_3$) δ: 1.20 (6H, t, —OCH$_2$CH$_3$×2), 1.38 (2H, t, —CO$_2$CH$_2$CH$_3$), 1.9 (4H, m, C$_6$ and C$_7$—H of naphthalene), 2.6–3.0 (6H, m, hydrogen of methylene and C$_8$—H of naphthalene), 3.6 (4H, q, —OCH$_2$CH$_3$×2), 4.33 (2H, q, —CO$_2$CH$_2$CH$_3$), 4.53 (1H, t, —CH(OC$_2$H$_5$)$_2$), 7.54 (1H, d, C$_4$—H of naphthalene), 7.71 (1H, s, C$_1$—H of naphthalene), 7.76 (1H, d, C$_3$—H of naphthalene).

(3) 2.5 g of the above product and 0.78 g of sodium thiocyanate were mixed with 35 ml of a 50% aqueous solution of ethanol and 0.7 ml of concentrated hydrochloric acid was added thereto. The mixture was heated to 100°–110° C. Water and ethanol were distilled off and the oily residue was extracted with chloroform. The extract was washed with water and dried and then concentrated in vacuo. The residue was purified by silica gel column chromatography to give 2.0 g of ethyl 5-((2-mercapto-1-imidazolyl)methyl)-5,6,7,8-tetrahydro-2-naphthalenecarboxylate as crystals with m.p. 155°–156° C.

Referential Example 11

(1) 11.8 g of potassium tertiary butoxide was added to 30 ml of dimethylformamide. The mixture was cooled in an ice-bath and then a mixture of 11.3 g of 7-bromo-1-oxo-1,2,3,4-tetrahydronaphthalene, 5 g of carbon disulfide and 30 ml of anhydrous benzene was added dropwise thereto under nitrogen gas. The resulting mixture was stirred at room temperature for 4 hours and 15 g of iodomethane was added thereto. The mixture was stirred at room temperature and then heated under reflux for 3 hours. After cooling, the reaction mixture was added to 300 ml of an ice-cold water and the mixture was stirred. The reaction mixture was extracted with benzene. The extract was washed with water and dried and then concentrated in vacuo. The residue was purified by column chromatography on 300 g of silica gel to give 10.5 g of 7-bromo-2-(bis(methylthio)methylene)-1-oxo-1,2,3,4-tetrahydronaphthalene as an oil.

(2) 10.5 g of the above product was dissolved in a mixture of 40 ml of chloroform and 80 ml of ethanol and then 6 g of sodium borohydride was added thereto. The mixture was heated under reflux for 1 hour and then 4 g of sodium borohydride was added thereto. The resulting mixture was heated under reflux for 1 hour. After cooling, the reaction mixture was concentrated in vacuo. Water was added to the residue and the mixture was extracted with chloroform. The extract was washed with water and dried and then concentrated in vacuo to give 10.3 g of 2-(bis(methylthio)methylene)-7-bromo-1-hydroxy-1,2,3,4-tetrahydronaphthalene as an oil.

(3) 10.3 g of the above product was mixed with 22 ml of boron trifluoride-diethyl ether complex, and the mixture was stirred at room temperature for 5 minutes. 70 ml of methanol was added to the mixture and the resulting mixture was heated under reflux for 18 hours. After cooling, the reaction mixture was concentrated in vacuo and water was added to the residue. The mixture was extracted with chloroform. The extract was washed with water and dried and then concentrated in vacuo to give 8 g of methyl 7-bromo-3,4-dihydro-2-naphthalenecarboxylate as an oil.

(4) The above product was allowed to react using procedures analogous to those described in steps (3), (4), (5), (6) and (7) of Referential Example 1 to give ethyl 7-(p-toluenesulfonyloxymethyl)-5,6,7,8-tetrahydro-2-naphthalenecarboxylate as an oil.

$^1$H-NMR (CDCl$_3$) δ: 1.38 (3H, t, —CO$_2$CH$_2$CH$_3$), 1.80–2.40 (3H, m, C$_6$ and C$_7$—H of naphthalene), 2.45 (3H, s, —CH$_3$), 2.30–3.04 (4H, m, C$_5$ and C$_6$—H of naphthalene), 4.00 (2H, d, —CH$_2$O—), 4.35 (2H, q, —CO$_2$CH$_2$CH$_3$), 7.00–7.92 (7H, m, hydrogene of aromatic ring).

Referential Example 12

(1) 11.7 g of 2,2-indandicarboxylic acid was heated at 200° C. for 30 minutes. After liberation of bubbles ceased, the reaction product was cooled and dissolved in 150 ml of ethanol. 4 ml of concentrated sulfuric acid was added to the solution and the mixture was heated under reflux for 4 hours. The reaction mixture was concentrated in vacuo and the residue was neutralized by addition of sodium carbonate. The mixture was extracted with chloroform. The extract was washed with water and dried and then concentrated in vacuo to give 9.4 g of ethyl 2-indancarboxylate as an oil.

(2) 3.5 g of the above product was dissolved in 50 ml of tertiary butanol and 1.75 g of sodium borohydride was added thereto. The mixture was heated under reflux and 10 ml of methanol was added dropwise to the refluxing mixture over a period of 1 hour and then the resulting mixture was heated under reflux for 1 hour. Water was added to the reaction mixture to decompose any excess sodium borohydride and the mixture was concentrated in vacuo. The residue was extracted with chloroform. The extract was washed with water, dried and then concentrated in vacuo to give 3.4 g of 2-(hydroxymethyl)indan.

(3) 142 g of the above product was allowed to react using a procedure analogous to that described in step (7) of Referential Example 1 to give 282 g of 2-(p-toluenesulfonyloxymethyl)indan as colorless crystals with m.p. 95°–97° C.

(4) 282 g of the above product was allowed to react using procedures analogous to those described in steps (2) and (3) of Referential Example 2 to give 123 g of ethyl 3-(2-indanyl)propionate as an oil with b.p. 137°–139° C./3 mmHg.

(5) 123 g of the above product was allowed to react using a pocedure analogous to that described in step (2) of this Referential Example to give 99 g of 2-(3-hydroxypropyl)indan as an oil.

(6) 155 g of the above product was dissolved in 1 liter of 1,2-dichloroethane. The solution was cooled in an ice-bath and 246 g of anhydrous aluminum chloride was added portionwise thereto. 99 ml of acetyl chloride was added dropwise to the mixture and the resulting mixture was stirred for 10 minutes. The reaction mixture was added to an ice-cold water, and 80 ml of concentrated hydrochloric acid was added thereto. The mixture was extracted with chloroform. The extract was washed with water and dried and then concentrated in vacuo. The oily residue was dissolved in 1.5 liters of dioxane and the solution was cooled in an ice-bath. To the solution was added dropwise at 10° C. an aqueous solution of sodium hypobromite prepared by adding dropwise 118 ml of bromine to an aqueous solution of 243 g of sodium hydroxide in 2 liters of water. The resulting mixture was stirred at a temperature not more than 10° C. for 1 hour and stirred at room temperature for 3 hours. Ethyl acetate was added to the reaction mixture. The aqueous layer was acidified with concentrated hydrochloric acid. The precipitate formed was collected by filtration.

800 ml of ethanol and 30 ml of concentrated sulfuric acid were added to the precipitate and the mixture was heated under reflux for 12 hours. The reaction mixture was concentrated in vacuo and the residual liquid was neutralized by addition of potassium carbonate. The mixture was extracted with ethyl acetate. The extract was washed with water, dried and then concentrated in vacuo. The residue was purified by column chromatography on 1.5 kg of silica gel to give 112 g of ethyl 2-(3-hydroxypropyl)-5-indancarboxylate as an oil.

(7) The above product was allowed to react using procedures analogous to those described in steps (5) and (6) of Referential Example 2 to give ethyl 2-(2-amino-5-thiazolylmethyl)-5-indancarboxylate as an oil.

$^1$H-NMR (CDCl$_3$) δ: 1.38 (3H, t, —CO$_2$CH$_2$CH$_3$), 2.61 (1H, m, C$_2$—H of indan), 2.76 (4H, m, C$_1$ and C$_3$—H of indan), 3.09 (2H, m,

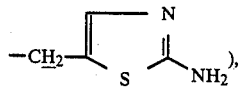), 4.36 (2H, q, —CO$_2$CH$_2$CH$_3$), 6.77 (1H, s, C$_4$—H of thiazole), 7.22 (1H, d, C$_7$—H of indan), 7.84 (1H, d, C$_6$—H of indan), 7.86 (1H, s, C$_4$—H of indane).

Referential Example 13

5.5 g of ethyl 5-bromo-2-indancarboxylate was allowed to react using procedures analogous to those described in steps (3), (4), (5), (6) and (7) of Referential Example 1 to give 2.5 g of ethyl 2-(p-toluenesulfonyloxymethyl)-5-indancarboxylate as an oil.

$^1$H-NMR (CDCl$_3$) δ: 1.37 (3H, t, —CO$_2$CH$_2$CH$_3$), 2.44 (3H, s, —CH$_3$), 2.5–3.2 (5H, m, C$_1$, C$_2$ and C$_3$—H of indan), 4.02 (2H, d, —CH$_2$OSO$_2$—), 4.35 (2H, q, —CO$_3$CH$_2$CH$_3$), 7.1–7.9 (7H, m, hydrogen of aromatic ring).

Referential Example 14

(1) 3.9 g of 5-bromo-2-indancarboxylic acid and 2 g of 2-amino-2-methyl-1-propanol were added to 100 ml of xylene. The mixture was heated under reflux for 24 hours while removing the water produced. The reaction mixture was concentrated in vacuo and 20 ml of water was added to the residue. The mixture was extracted with chloroform. The extract was washed with water, dried and then concentrated in vacuo. The residue was purified by silica gel column chromatography to give 3 g of 2-(5-bromoindan-2-yl)-4,4-dimethyloxazoline as an oil.

(2) 3 g of the above product and 2.2 g of bromoethane were dissolved in 30 ml of tetrahydrofuran. The solution was added dropwise to a refluxing solution of 0.7 g of magnesium in 10 ml of tetrahydrofuran under nitrogen gas. The mixture was heated under reflux for 1 hour. The reaction mixture was cooled in an ice-bath and a mixture of 3 g of dimethylformamide and 10 ml of tetrahydrofuran was added dropwise thereto. The resulting mixture was stirred at room temperature for 30 minutes and heated for 1 hour. After cooling, a saturated aqueous solution or ammonium chloride was added to the reaction mixture and the mixture was extracted with 50 ml of ethyl acetate. The extract was dried and concentrated in vacuo. The residue was purified by column chromatography on 30 g of silica gel to give 1.0 g of 2-(4,4-dimethyloxazoline-2-yl)-5-indanaldehyde as an oil.

(3) 1.0 g of the above product was mixed with 50 ml of ethanol and 2 ml of concentrated sulfuric acid and the mixture was heated under reflux for 4 hours. The reaction mixture was concentrated in vacuo and 50 ml of an ice-cold water was added to the residue. The mixture was extracted with 100 ml of chloroform and the extract was concentrated in vacuo. The residue was purified by column chromatography on 30 g of silica gel to give 0.5 g of ethyl 5-formyl-2-indancarboxylate as an oil.

$^1$H-NMR (CDCl$_3$) δ: 1.29 (3H, t, —CO$_2$CH$_2$CH$_3$), 3.3 (5H, m, C$_1$, C$_2$ and C$_3$—H of indan), 4.19 (2H, q, —CO$_2$CH$_2$CH$_3$), 7.35 (1H, d, C$_7$—H of indan), 7.69 (1H, d, C$_6$—H of indan), 7.73 (1H, s, C$_4$—H of indan), 9.96 (1H, s, —CHO).

(4) 0.5 g of the above product was dissolved in 30 ml of ethanol and 0.1 g of sodium borohydride was added to the solution. The mixture was stirred at room temperature for 2 hours. The reaction mixture was concentrated in vacuo and 20 ml of water was added to the residue. The mixture was stirred and extracted with 50 ml of chloroform. The extract was dried and concentrated in vacuo to give 0.4 g of ethyl 5-(hydroxymethyl)-2-indancarboxylate as an oil.

(5) 400 mg of the above product was allowed to react using a procedure analogous to that described in step (4) of Referential Example 5 to give ethyl 5-(chloromethyl)-2-indancarboxylate as a crude product.

EXAMPLE 1

0.56 g of 50% sodium hydride was suspended in 60 ml of anhydrous dimethylformamide, and 0.79 g of imidazole was added thereto. The mixture was stirred at room temperature for 20 minutes and 4.5 g of ethyl 6-(p-toluenesulfonyloxymethyl)-5,6,7,8-tetrahydro-2-naphthalenecarboxylate was added portionwise thereto. The resulting mixture was stirred at room temperature for 3 days. The reaction mixture was concentrated in vacuo and the residue was extracted with chloroform. The extract was washed with water and dried over sodium sulfate and then concentrated in vacuo. The residue was purified by silica gel column chromatography using a mixture of methanol and chloroform (2:98 by volume) for elution to give 2.31 g of ethyl 6-(1-imidazolylmethyl)-5,6,7,8-tetrahydro-2-naphthalenecarboxylate as a colorless oil.

$^1$-NMR (CDCl$_3$) δ: 1.37 (3H, t, —CO$_2$CH$_2$CH$_3$), 3.94 (2H, d,

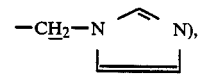), 4.35 (2H, q, —CO$_2$CH$_2$CH$_3$), 6.93 (1H, s, C$_2$—H of imidazole), 7.08 (1H, s, C$_4$—H of imidazole), 7.48 (1H, s, C$_5$—H of imidazole), 7.7–7.8 (2H, m, C$_5$ and C$_7$—H of naphthalene).

EXAMPLE 2

A mixture of 2.31 g of ethyl 6-(1-imidazolylmethyl)-5,6,7,8-tetrahydro-2-naphthalenecarboxylate, 0.49 g of sodium hydroxide, 60 ml of methanol and 20 ml of water was heated under reflux for 4 hours. Methanol was distilled off in vacuo and 50 ml of water was added to the residue. Chloroform was added to the mixture and the aqueous layer was separated. The aqueous solution was adjusted to pH 6 with 2 normal hydrochloric acid. The precipitate formed was collected by filtration and washed with water to give 1.14 g of 6-(1-imidazolylmethyl)-5,6,7,8-tetrahydro-2-naphthalenecarboxylic acid as a colorless powder with m.p. 224°–226° C.

1.14 g of the above product was suspended in a small amount of ethanol and concentrated hydrochloric acid was added thereto. The mixture was concentrated to dryness in vacuo. The residue was recrystallized from a mixture of ethanol and diethyl ether to give 1.05 g of a hydrochloric acid addition salt of the above product as a colorless powder with m.p. 240°–252° C.

Analysis for $C_{15}H_{16}N_2O_2 \cdot HCl$: Calcd: C: 61.54, H: 5.85, N: 9.57, Found: C: 61.30, H: 5.84, N: 9.50.

EXAMPLE 3

2.1 g of ethyl 6-(2-amino-5-thiazolylmethyl)-5,6,7,8-tetrahydro-2-naphthalenecarboxylate was dissolved in 23 ml of phosphoric acid and 12 ml of concentrated nitric acid was added thereto. A solution of 0.46 g of sodium nitrite in 4 ml of water was added dropwise to the mixture. The resulting mixture was stirred at −8° C. for 20 minutes. The reaction mixture was added to a solution of 5.28 g of cuprous chloride in 7 ml of concentrated hydrochloric acid at −5° C. The resulting mixture was stirred at −8° to 0° C. for 1.5 hours and 100 ml of an ice-cold water was added thereto. The mixture was neutralized by adding sodium carbonate and the resulting mixture was extracted with chloroform. The extract was washed with water and dried and then concentrated in vacuo. The residue was dissolved in 15 ml of acetic acid and 14.4 g of zinc powder was added portionwise thereto under heating. The mixture was heated under reflux for 2 hours. After cooling, the insoluble material was removed by filtration. The filtrate was concentrated in vacuo and the residue was dissolved in chloroform. The solution was washed with water, dried and concentrated in vacuo. The residue was purified by silica gel column chromatography using a mixture of methanol and chloroform (2:98 by volume) for elution to give 1.27 g of ethyl 6-(5-thiazolylmethyl)-5,6,7,8-tetrahydro-2-naphthalenecarboxylate as an oil.

$^1$H-NMR (CDCl$_3$) δ: 1.37 (3H, t, $-CO_2CH_2C\underline{H}_3$), 4.34 (2H, q, $-CO_2C\underline{H}_2CH_3$), 7.05 (1H, d, $C_4-\underline{H}$ of naphthalene), 7.60 (1$\underline{H}$, s, $C_4-H$ of thiazole), 7.60–7.70 (2H, m, $C_1$ and $C_3-H$ of naphthalene), 8.68 (1H, s, $C_2-H$ of thiazole).

In addition to the above signals, signals for $C_5$, $C_6$, $C_7$ and $C_8-H$ of naphthalene and hydrogen of methylene group substituted at 6-position of naphthalene were found in 2–4 ppm.

EXAMPLE 4

3.92 g of ethyl 6-(5-thiazolylmethyl)-5,6,7,8-tetrahydro-2-naphthalenecarboxylate was added to a mixture of 10 ml of a 10% aqueous solution of sodium hydroxide and 30 ml of methanol and the mixture was heated under reflux for 1 hour. The reaction mixture was concentrated to dryness in vacuo and the residue was dissolved in water. A small amount of insoluble material was removed by filtration and the filtrate was adjusted to pH 6 with hydrochloric acid. The precipitate formed was collected by filtration to give 2.71 g of 6-(5-thiazolylmethyl)-5,6,7,8-tetrahydro-2-naphthalenecarboxylic acid as a powder. The powder was suspended in 20 ml of water and 0.42 g of sodium hydroxide was added thereto. The insoluble material was removed by filtration and the filtrate was concentrated in vacuo. The residue was recrystallized from a mixture of ethanol and diethyl ether to give 1.92 g of sodium carboxylate of the above product as a colorless powder with m.p. above 280° C.

Analysis for $C_{15}H_{14}NO_2SNa$: Calcd: C: 61.00, H: 4.77, N: 4.74, Found: C: 60.95, H: 4.91, N: 4.73.

$^1$H-NMR (D$_2$O) δ: 6.99 (1H, d, J=8 Hz, $C_4-H$ of naphthalene), 8.4–8.7 (3H, m, $C_1$ and $C_3-H$ of naphthalene and $C_4-H$ of thiazole), 8.73 (1H, s, $C_2-H$ of thiazole).

In addition to the above signals, signals for $C_5$, $C_6$, $C_7$ and $C_8-H$ of naphthalene and hydrogens of methylene group substituted at 6-position of naphthalene were found in 1.5–4 ppm.

EXAMPLE 5

0.87 g of cupric chloride was suspended in 20 ml of acetonitrile and 0.82 g of tertiary butyl nitrite was added thereto. A solution of 1.8 g of ethyl 5-(2-(2-amino-thiazole-5-yl)ethyl)-5,6,7,8-tetrahydro-1-naphthalenecarboxylate in 5 ml of acetonitrile was added dropwise to the mixture. After evolution of gas ceased, 15% hydrochloric acid was added to the mixture. The resulting mixture was extracted with chloroform. The extract was washed with water, dried and then concentrated in vacuo. The residue was purified by silica gel column chromatography with chloroform eluent to give an oily product. The product was dissolved in 30 ml of acetic acid, and a small amount of zinc powder was added thereto under refluxing. The above procedure was repeated four times at hourly intervals and the total amount of zinc was 0.4 g. The insoluble material was removed by filtration and the filtrate was concentrated in vacuo. The residue was dissolved in chloroform. The solution was washed with water and dried and then concentrated in vacuo. The residue was purified by silica gel column chromatography to give 1.3 g of ethyl 5-(2-(5-thiazolyl)ethyl)-5,6,7,8-tetrahydro-1-naphthalenecarboxylate as an oil.

$^1$H-NMR (CDCl$_3$) δ: 1.37 (3H, t, $-CO_2CH_2C\underline{H}_3$), 1.6–2.2 (6H, m, hydrogen of methylene), 2.8 (1$\underline{H}$, m, $C_5-H$ of naphthalene), 2.95 (4H, t, hydrogen of methylene and $C_8-H$ of naphthalene), 4.34 (2H, q, $-CO_2C\underline{H}_2CH_3$), 7.0–7.4 (2H, m, $C_3$ and $C_4-H$ of naphthalene), 7.62 (2H, m, $C_4-H$ of thiazole and $C_2-H$ of naphthalene), 8.66 (1H, s, $C_2-H$ of thiazole).

EXAMPLE 6

1.3 g of ethyl 5-(2-(5-thiazolyl)ethyl)-5,6,7,8-tetrahydro-1-naphthalenecarboxylate was allowed to react using a procedure analogous to that described in Example 4 to give 0.39 g of sodium 5-(2-(5-thiazolyl)ethyl)-5,6,7,8-tetrahydro-1-naphthalenecarboxylate as a colorless powder with m.p. 104°–115° C.

Analysis for $C_{16}H_{16}NO_2SNa$: Calcd: C: 62.12, H: 5.21, N: 4.53, Found: C: 61.48, H: 5.33, N: 4.57.

$^1$H-NMR (D$_2$O) δ: 1.5–2.1 (6H, m, hydrogen of methylene), 2.5–3.1 (5H, m, $C_5$ and $C_8-H$ of naphthalene and

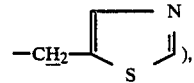

7.0–7.3 (3H, m, $C_2$, $C_3$ and $C_4-H$ on naphthalene), 7.53 (1H, s, $C_4-H$ of thiazole), 8.70 (1H, s, $C_2-H$ of thiazole).

EXAMPLE 7

A mixture of 0.49 g of tertiary butyl nitrite and 5 ml of dimethylformamide was heated at 50° C. and then 1.0 g of ethyl 6-(2-amino-5-thiazolylmethyl)-1,2,3,4-tetrahydro-2-naphthalenecarboxylate was added portionwise thereto. The resulting mixture was stirred at 60° C. for 1 hour. After cooling, ethyl acetate was added to the reaction mixture and the mixture was washed with water and dried and then concentrated in vacuo. The residue was purified by silica gel column chromatography using a mixture of methanol and chloroform (1:50 by volume) for elution to give 720 mg of ethyl 6-(5-thiazolylmethyl)-1,2,3,4-tetrahydro-2-naphthalenecarboxylate as an oil.

$^1$H-NMR (CDCl$_3$) δ: 1.26 (3H, t, —CO$_2$CH$_2$C$\underline{H}$$_3$), 1.6–2.4 (2H, m, C$_3$—H of naphthalene), 2.5–3.1 (5H, m, C$_1$, C$_2$ and C$_4$—H of naphthalene), 3.86 (2H, s, hydrogen of methylene), 4.15 (2H, q, —CO$_2$C$\underline{H}$$_2$CH$_3$), 6.8–7.1 (3H, m, C$_5$, C$_7$ and C$_8$—H of naphthalene), 7.85 (1H, s, C$_4$—H of thiazole), 8.71 (1H, s, C$_2$—H of thiazole).

EXAMPLE 8

720 mg of ethyl 6-(5-thiazolylmethyl)-1,2,3,4-tetrahydro-2-naphthalenecarboxylate was allowed to react using a procedure analogous to that described in Example 4 to give 145 mg of sodium 6-(5-thiazolylmethyl)-1,2,3,4-tetrahydro-2-naphthalenecarboxylate with m.p. 256°–262° C. as a colorless powder.

Analysis for C$_{15}$H$_{14}$NO$_2$SNa: Calcd: C: 61.00, H: 4.78, N: 4.74, Found: C: 60.95, H: 4.91, N: 4.73.

$^1$H-NMR (D$_2$O) δ: 1.5–2.8 (7H, m, C$_1$, C$_2$, C$_3$ and C$_4$—H of naphthalene), 4.03 (2H, s,

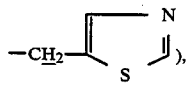

6.90–7.10 (3H, m, C$_5$, C$_7$ and C$_8$—H of naphthalene), 7.85 (1H, s, C$_4$—H of thiazole), 8.72 (1H, s, C$_2$—H of thiazole).

EXAMPLE 9

The crude ethyl 6-(chloromethyl)-1,2,3,4-tetrahydro-2-naphthalenecarboxylate obtained in Referential Example 5 was dissolved in 100 ml of anhydrous acetonitrile and then 3.22 g of sodium iodide and 3.94 g of 1-acetylimidazole were added thereto. The resulting mixture was heated under reflux for 1.5 hours. The reaction mixture was concentrated in vacuo and 100 ml of methanol was added to the residue. The mixture was stirred and concentrated in vacuo. Water was added to the residue. The mixture was neutralized by adding sodium bicarbonate and extracted with chloroform. The extract was washed with water, dried and then concentrated in vacuo. The residue was purified by silica gel column chromatography using a mixture of ethanol and chloroform (3:97 by volume) for elution to give an oily product. The product was suspended in ethanol, and an ethanolic solution of hydrogen chloride was added thereto. The mixure was concentrated to dryness in vacuo to give 4.8 g of ethyl 6-(1-imidazolylmethyl)-1,2,3,4-tetrahydro-2-naphthalenecarboxylate hydrochloride as colorless crystals with m.p. 170°–172° C.

$^1$H-NMR (dimethyl sulfoxide-d$_6$ (hereinafter abbreviated as DMSO-d$_6$)) δ: 1.19 (3H, t, —CO$_2$CH$_2$C$\underline{H}$$_3$), 1.5–3.0 (7H, m, C$_1$, C$_2$, C$_3$ and C$_4$—H of naphthalene), 4.1 (2H, q, —CO$_2$C$\underline{H}$$_2$CH$_3$), 5.37 (2H, s,

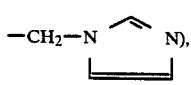

7.16 (3H, s, C$_5$, C$_7$ and C$_8$—H of naphthalene), 7.67 (1H, t, C$_4$—H of imidazole), 7.79 (1H, t, C$_5$—H of imidazole), 9.37 (1H, s, C$_2$—H of imidazole).

EXAMPLE 10

4.5 g of ethyl 6-(1-imidazolylmethyl)-1,2,3,4-tetrahydro-2-naphthalenecarboxylate hydrochloride was added to a mixture of 15 ml of concentrated hydrochloric acid and 30 ml of methanol and then the mixture was heated under reflux for 20 hours. The reaction mixture was concentrated in vacuo to give 2.52 g of 6-(1-imidazolylmethyl)-1,2,3,4-tetrahydro-2-naphthalenecarboxylic acid hydrochloride as colorless prisms with m.p. 193°–223° C.

Analysis for C$_{15}$H$_{16}$N$_2$O$_2$.HCl: Calcd: C: 61.54, H: 5.85, N: 9.57, Found: C: 61.51, H: 5.67, N: 9.19.

$^1$H-NMR (D$_2$O) δ: 1.5–3.1 (7H, m, C$_1$, C$_2$, C$_3$ and C$_4$—H of naphthalene), 5.30 (2H, s,

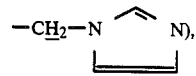

7.13 (3H, s, C$_5$, C$_7$ and C$_8$—H of naphthalene), 7.41 (1H, s, C$_4$ or C$_5$—H of imidazole), 7.43 (1H, s, C$_5$ or C$_4$—H of imidazloe), 8.73 (1H, s, C$_2$—H of imidazole).

EXAMPLE 11

1.8 g of ethyl 2-(6-(chloromethyl)-1,2,3,4-tetrahydro-1-naphthyl)acetate was allowed to react using a procedure analogous to that described in Example 9 to give 0.68 g of ethyl 2-(6-(1-imidazolylmethyl)-1,2,3,4-tetrahydro-1-naphthyl)acetate as an oil.

$^1$H-NMR (CDCl$_3$) δ: 1.26 (3H, t, —CO$_2$CH$_2$C$\underline{H}$$_3$), 1.8 (4H, m, C$_2$ and C$_3$—H of naphthalene), 2.3–2.6 (2H, m, —C$\underline{H}$$_2$CO$_2$—), 2.7 (2H, m, C$_4$—H of naphthalene), 3.3 (1H, m, C$_1$—H of naphthalene), 4.14 (2H, q, —CO$_2$C$\underline{H}$$_2$CH$_3$), 5.0 (2H, s, —C$\underline{H}$$_2$—), 6.8–6.9 (3H, m, C$_5$, C$_7$ and C$_8$—H of naphthalene), 7.05 (2H, m, C$_4$ and C$_5$—H of imidazole), 7.47 (1H, s, C$_2$—H of imidazole).

EXAMPLE 12

0.65 g of ethyl 2-(6-(1-imidazolylmethyl)-1,2,3,4-tetrahydro-1-naphthyl)acetate was added to a mixture of 7 ml of ethanol, 7 ml of water and 0.28 g of sodium hyrdoxide and then the mixture was heated under reflux for 1 hour. The reaction mixture was concentrated in vacuo and the residue was adjusted to pH 2 with concentrated hydrochloric acid and then the mixture was concentrated to dryness in vacuo. The residue was treated with ethanol at room temperature and the insoluble inorganic salt was removed by filtration. The filtrate was concentrated to dryness in vacuo and the residue was crystallized from a mixture of water and acetone to give 0.48 g of 2-(6-(1-imidazolylmethyl)-1,2,3,4-tetrahydro-1-naphthyl)acetic acid hydrochloride as colorless crystals with m.p. 189°–190° C.

Analysis for C$_{16}$H$_{18}$N$_2$O$_2$.HCl: Calcd: C: 62.64, H: 6.24, N: 9.13, Found: C: 62.74, H: 6.08, N: 8.98.

$^1$H-NMR (D$_2$O) δ: 1.6 (4H, m, C$_2$ and C$_3$—H of naphthalene), 2.1–2.8 (4H, m, C$_4$—H of naphthalene and —C$\underline{H}$$_2$CO$_2$), 3.05 (1H, m, C$_1$—H of naphthalene), 5.28 (2H, s,

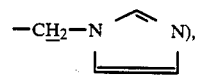

7.09 (3H, s, C$_5$, C$_7$ and C$_8$—H of naphthalene), 7.4 (2H, d, C$_4$ and C$_5$—H of imidazole), 8.75 (1H, s, C$_2$—H of imidazole).

EXAMPLE 13

1.8 g of ethyl 6-(3-pyridylmethyl)-7,8-dihydro-2-naphthalenecarboxylate was dissolved in 100 ml of ethanol and 1 g of 10% palladium carbon was added thereto. The mixture was catalytically reduced. After absorption of hydrogen gas was completed, the catalyst was removed by filtration. The filtrate was concentrated in vacuo to give 1.8 g of ethyl 6-(3-pyridylmethyl)-5,6,7,8-tetrahydro-2-naphthalenecarboxylate as an oil.

$^1$H-NMR (CDCl$_3$) δ: 1.36 (3H, t, —CO$_2$CH$_2$C$\underline{H}_3$), 1.8–2.3 (2H, m, C$_7$—H of naphthalene), 2.4–3.3 (7H, m, C$_5$, C$_6$ and C$_8$—H of naphthalene and hydrogen of methylene), 4.32 (2H, q, —CO$_2$C$\underline{H}_2$CH$_3$), 7.0–8.5 (7H, m, hydrogen of aromatic ring).

EXAMPLE 14

1.8 g of ethyl 6-(3-pyridylmethyl)-5,6,7,8-tetrahydro-2-naphthalenecarboxylate was mixed with 50 ml of 6 normal hydrochloric acid and the mixture was heated under reflux for 4 hours. The reaction mixture was concentrated to dryness in vacuo. The residue was recrystallized from methanol to give 1.04 g of 6-(3-pyridylmethyl)-5,6,7,8-tetrahydro-2-naphthalenecarboxylic acid hydrochloride as colorless crystals with m.p. 222°–226° C.

$^1$H-NMR (DMSO-d$_6$) δ: 1.8–2.2 (2H, m, C$_7$—H of naphthalene), 2.4–3.3 (7H, m, C$_5$, C$_6$ and C$_8$—H of naphthalene and hydrogen of methylene), 7.1–8.9 (7H, m, hydrogen of aromatic ring).

Analysis for C$_{17}$H$_{17}$NO$_2$.HCl: Calcd: C: 67.21, H: 5.97, N: 4.61, Found: C: 67.17, H: 6.02, N: 4.55.

EXAMPLE 15

2.1 g of ethyl 5-(2-(p-toluenesulfonyloxy)ethyl)-5,6,7,8-tetrahydro-2-naphthalenecarboxylate was allowed to react using a procedure analogous to that described in Example 1 to give 1.2 g of ethyl 5-(2-(1-imidazolyl)ethyl)-5,6,7,8-tetrahydro-2-naphthalenecarboxylate as an oil.

$^1$H-NMR (CDCl$_3$) δ: 1.36 (3H, t, —CO$_2$CH$_2$C$\underline{H}_3$), 2.6–3.0 (3H, m, C$_5$ and C$_8$—H of naphthalene), 3.99 (2H, t, hydrogen of methylene), 4.32 (2H, q, —CO$_2$C$\underline{H}_2$CH$_3$), 6.90 (1H, s, C$_5$—H of imidazole), 7.02 (1H, s, C$_4$—H of imidazole), 7.04 (1H, d, C$_4$—H of naphthalene), 7.70 (1H, s, C$_1$—H of naphthalene), 7.72 (1H, d, C$_3$—H of naphthalene).

EXAMPLE 16

1.2 g of ethyl 5-(2-(1-imidazolyl)ethyl)-5,6,7,8-tetrahydro-2-naphthalenecarboxylate was allowed to react using a procedure analogous to that described in Example 12 to give 0.7 g of 5-(2-(1-imidazolyl)ethyl)-5,6,7,8-tetrahydro-2-naphthalenecarboxylic acid hydrochloride as colorless crystals with m.p. 242°–244° C.

$^1$H-NMR (DMSO-d$_6$) δ: 1.4–2.2 (4H, m, C$_6$ and C$_7$—H of naphthalene), 2.6 (2H, m, C$_8$—H of naphthalene), 2.8 (1H, m, C$_5$—H of naphthalene), 4.8 (2H, m, hydrogen of methylene), 7.10 (1H, d, C$_4$—H of naphthalene), 7.42 (1H, m, C$_5$—H of imidazole), 7.48 (1H, m, C$_4$—H of imidazole), 7.56 (1H, m, C$_1$—H of naphthalene), 7.62 (1H, m, C$_3$—H of naphthalene), 8.65 (1H, m, C$_2$—H of imidazole).

Analysis for C$_{16}$H$_{18}$N$_2$O$_2$.HCl; Calcd: C: 62.64, H: 6.24, N: 9.13, Found: C: 62.81, H: 6.24, N: 9.07.

EXAMPLE 17

4.1 g of ethyl 5-(2-(p-toluenesulfonyloxy)ethyl)-5,6,7,8-tetrahydro-1-naphthalenecarboxylate was allowed to react using a procedure analogous to that described in Example 1 to give 1.7 g of ethyl 5-(2-(1-imidazolyl)ethyl)-5,6,7,8-tetrahydro-1-naphthalenecarboxylate as an oil.

$^1$H-NMR (CDCl$_3$) δ: 1.37 (3H, t, —CO$_2$CH$_2$C$\underline{H}_3$), 1.56–1.96 (4H, m, C$_6$ and C$_7$—H of naphthalene), 1.96—2.32 (2H, m,

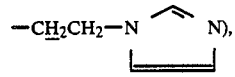

2.70–3.20 (3H, m, C$_5$ and C$_8$—H of naphthalene), 4.02 (2H, t,

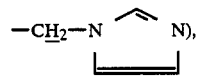

4.34 (2H, q, —CO$_2$C$\underline{H}_2$CH$_3$), 6.92–7.80 (6H, m, hydrogen of aromatic ring).

EXAMPLE 18

1.7 g of ethyl 5-(2-(1-imidazolyl)ethyl)-5,6,7,8-tetrahydro-1-naphthalenecarboxylate was allowed to react using a procedure analogous to that described in Example 12 to give 1.2 g of 5-(2-(1-imidazolyl)ethyl)-5,6,7,8-tetrahydro-1-naphthalenecarboxylic acid hydrochloride as colorless crystals with m.p. 219.5°–220.5° C.

$^1$H-NMR (DMSO-d$_6$) δ: 1.50–2.00 (4H, m, C$_6$ and C$_7$—H of naphthalene), 2.00–2.40 (2H, m,

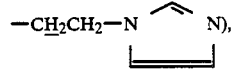

2.64–3.12 (3H, m, C$_5$ and C$_8$—H of naphthalene), 4.36 (2H, t,

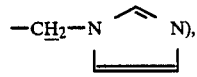

7.22 (1H, t, C$_3$—H of naphthalene), 7.42 (1H, dd, C$_4$—H of naphthalene), 7.49 (1H, dd, C$_2$—H of naphthalene), 7.63 (2H, m, C$_4$ and C$_5$—H of imidazole), 9.36 (1H, m, C$_2$—H of imidazole).

Analysis for C$_{16}$H$_{18}$N$_2$O$_2$.HCl: Calcd: C: 62.64, H: 6.24, N: 9.13, Found: C: 62.30, H: 6.41, N: 9.09.

EXAMPLE 19

1.74 g of ethyl 5-((2-mercapto-1-imidazolyl)methyl)-5,6,7,8-tetrahydro-2-naphthalenecarboxylate was mixed with 50 ml of acetic acid, 15 ml of concentrated nitric acid, 15 ml of water and 15 mg of sodium nitrite, and then the mixture was stirred at 40°–50° C. for 4 hours. The reaction mixture was concentrated in vacuo and the residue was adjusted to pH 5–6 with an aqueous solution of sodium hydroxide. The mixture was extracted with chloroform. The extract was washed with water, dried and then concentrated in vacuo. The residue was purified by silica gel column chromatography to give 0.48 g of ethyl 5-(1-imidazolylmethyl)-5,6,7,8-tetrahydro-2-naphthalenecarboxylate as an oil.

¹H-NMR (CDCl₃) δ: 1.38 (3H, t, —CO₂CH₂C$\underline{H}$₃), 1.6–2.1 (4H, m, C₆ and C₇—H of naphthalene), 2.8 (2H, m, C₈—H of naphthalene), 4.16 (2H, s,

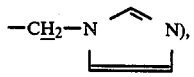

4.32 (2H, q, —CO₂C$\underline{H}$₂CH₃), 6.8 (2H, m, C₄ and C₅—H of imidazole), 7.24 (1H, s, C₂—H of imidazole), 7.44 (1H, d, C₄—H of naphthalene), 7.70 (1H, s, C₁—H of naphthalene), 7.75 (1H, d, C₃—H of naphthalene).

EXAMPLE 20

0.48 g of ethyl 5-(1-imidazolylmethyl)-5,6,7,8-tetrahydro-2-naphthalenecarboxylate was allowed to react using a procedure analogous to that described in Example 12 to give 0.16 g of 5-(1-imidazolylmethyl)-5,6,7,8-tetrahydro-2-naphthalenecarboxylic acid hydrochloride hydrate as crystals with m.p. 247°–248° C.

¹H-NMR (DMSO-d₆) δ: 1.5–2.0 (4H, m, C₆ and C₇—H of naphthalene), 2.8 (2H, m, C₈—H of naphthalene), 4.41 (2H, m,

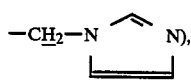

7.43 (1H, d, C₄—H of naphthalene), 7.6 (4H, m, C₁ and C₃—H of naphthalene and C₄ and C₅—H of imidazole), 9.0 (1H, s, C₂—H of imidazole).

Analysis for C₁₅H₁₆N₂O₂·HCl·H₂O: Calcd: C: 57.97, H: 6.16, N: 9.01, Found: C: 57.81, H: 5.81, N: 8.96.

EXAMPLE 21

8.7 g of ethyl 7-(p-toluenesulfonyloxymethyl)-5,6,7,8-tetrahydro-2-naphthalenocarboxylate was allowed to react using a procedure analogous to that described in Example 1 to give 2 g of ethyl 7-(1-imidazolylmethyl)-5,6,7,8-tetrahydro-2-naphthalenecarboxylate as an oil.

¹H-NMR (CDCl₃) δ: 1.38 (3H, t, —CO₂CH₂C$\underline{H}$₃), 1.50–3.10 (7H, m, C₅, C₆, C₇ and C₈—H of naphthalene), 3.95 (2H, m,

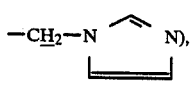

4.35 (2H, q, —CO₂C$\underline{H}$₂CH₃), 6.90–7.88 (6H, m, C₁, C₃ and C₄—H of naphthalene and C₂, C₄ and C₅—H of imidazole).

EXAMPLE 22

2 g of ethyl 7-(1-imidazolylmethyl)-5,6,7,8-tetrahydro-2-naphthalenecarboxylate was allowed to react using a procedure analogous to that described in Example 2 to give 1.2 g of 7-(1-imidazolylmethyl)-5,6,7,8-tetrahydro-2-naphthalenecarboxylic acid hydrochloride hemihydrate as colorless crystals with m.p. 269°–271° C.

¹H-NMR (DMSO-d₆) δ: 1.20–2.20 (3H, m, C₆ and C₇—H of naphthalene), 2.64–3.04 (4H, m, C₅ and C₈—H of naphthalene), 4.26 (2H, d,

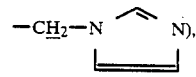

7.22 (1H, d, C₄—H of naphthalene), 7.60–7.96 (4H, m, C₁ and C₃—H of naphthalene and C₄ and C₅—H of imidazole), 9.28 (1H, s, C₂—H of imidazole).

Analysis of C₁₅H₁₆N₂O₂·HCl·½H₂O: Calcd: C: 59.70, H: 6.01, N: 9.28, Found: C: 60.02, H: 5.82, N: 9.20.

EXAMPLE 23

50 g of ethyl 2-(2-amino-5-thiazolylmethyl)-5-indancarboxylate was allowed to react using a procedure analogous to that described in Example 5 to give 27 g of ethyl 2-(5-thiazolylmethyl)-5-indancarboxylate as colorless crystals with m.p. 47°–49° C.

¹H-NMR (CDCl₃) δ: 1.38 (3H, t, —CO₂CH₂C$\underline{H}$₃), 2.6–3.4 (7H, m, C₁, C₂ and C₃—H of indan and

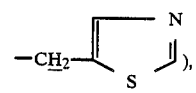

4.36 (2H, q, —CO₂C$\underline{H}$₂CH₃), 7.22 (1H, d, C₇—H of indan), 7.46 (1H, s, C₄—H of thiazole), 7.87 (1H, m, C₄ and C₆—H of indan), 8.70 (1H, s, C₂—H of thiazole).

EXAMPLE 24

27 g of ethyl 2-(5-thiazolylmethyl)-5-indancarboxylate was allowed to react using a procedure analogous to that described in Example 4 to give 16.4 g of sodium 2-(5-thiazolylmethyl)-5-indancarboxylate as crystals with m.p. 267°–280° C.

¹H-NMR (D₂O) δ: 2.3–3.2 (7H, m, C₁, C₂ and C₃—H of indan and

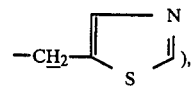

7.13 (1H, d, C₇—H of indan), 7.51 (1H, s, C₄—H of thiazole), 7.68 (1H, s, C₄—H of indan), 7.68 (1H, d, C₆—H of indan), 8.73 (1H, s, C₂—H of thiazole).

Analysis for C₁₄H₁₂NO₂SNa: Calcd: C: 59.77, H: 4.30, N: 4.98, Found: C: 58.99, H: 4.27, N: 4.92.

EXAMPLE 25

2.5 g of ethyl 2-(p-toluenesulfonyloxymethyl)-5-indancarboxylate was allowed to react using a procedure analogous to that described in Example 1 to give 1.3 g of ethyl 2-(1-imidazolylmethyl)-5-indancarboxylate as an oil.

¹H-NMR (CDCl₃) δ: 1.38 (3H, t, —CO₂CH₂C$\underline{H}$₃), 2.4–3.33 (5H, m, C₁, C₂ and C₃—H of indan), 3.98 (2H, d,

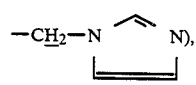

4.36 (2H, q, —CO$_2$CH$_2$CH$_3$), 6.95 (1H, s, C$_4$ or C$_5$—H of imidazole), 7.09 (1H, s, C$_5$ or C$_4$—H of imidazole), 7.24 (1H, d, C$_7$—H of indan), 7.49 (1H, s, C$_2$—H of imidazole), 7.87 (1H, d, C$_6$—H of indan), 7.87 (1H, s, C$_4$—H of indan).

EXAMPLE 26

1.3 g of ethyl 2-(1-imidazolylmethyl)-5-indancarboxylate was allowed to react using a procedure analogaous to that described in Example 2 to give 750 mg of 2-(1-imidazolylmethyl)-5-indancarboxylic acid hydrochloride as crystals with m.p. 258°–262° C.

$^1$H-NMR (DMSO-d$_6$) δ: 2.6–3.3 (5H, m, C$_1$, C$_2$ and C$_3$—H of indan), 4.35 (2H, d,

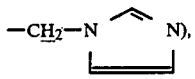

7.32 (1H, d, C$_7$—H of indan), 7.7–7.93 (4H, m, C$_4$, C$_6$—H of indan and C$_4$, C$_5$—H of imidazole), 9.25 (1H, s, C$_2$—H of imidazole).

Analysis for C$_{14}$H$_{14}$N$_2$O$_2$.HCl: Calcd: C: 60.33, H: 5.42, N: 10.05, Found: C: 60.51, H: 5.45, N: 10.01.

EXAMPLE 27

The crude ethyl 5-(chloromethyl)-2-indancarboxylate obtained in Referential Example 14 was allowed to react using a procedure analogous to that described in Example 9 to give 300 mg of ethyl 5-(1-imidazolylmethyl)-2-indancarboxylate as an oil.

$^1$H-NMR (CDCl$_3$) δ: 1.27 (3H, t, —CO$_2$CH$_2$CH$_3$), 3.0–3.3 (5H, m, C$_1$, C$_2$ and C$_3$—H of indan), 4.17 (2H, q, —CO$_2$CH$_2$CH$_3$), 5.07 (2H, s,

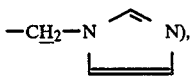

6.89 (1H, s, C$_4$ or C$_5$—H of imidazole), 6.99 (1H, s, C$_5$ or C$_4$—H of imidazole), 7.07 (1H, s, C$_4$—H of indan), 6.94 (1H, d, C$_7$—H of indan), 7.10 (1H, d, C$_6$—H of indan), 7.53 (1H, s, C$_2$—H of imidazole).

EXAMPLE 28

300 mg of ethyl 5-(1-imidazolylmethyl)-2-indancarboxylate was allowed to react using a procedure analogous to that described in Example 2 to give 250 mg of 5-(1-imidazolylmethyl)-2-indancarboxylic acid hydrochloride as colorless crystals with m.p. 186°–189° C.

$^1$H-NMR (DMSO-d$_6$) δ: 3.0–3.3 (5H, m, C$_1$, C$_2$ and C$_3$—H of indan), 5.38 (2H, s,

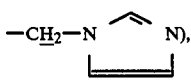

7.24 (2H, s, C$_6$ and C$_7$—H of indan), 7.29 (1H, s, C$_4$—H of indan), 7.67 (1H, t, C$_4$ or C$_5$—H of imidazole), 7.77 (1H, t, C$_5$ or C$_4$—H of imidazole), 9.29 (1H, s, C$_2$—H of imidazole).

Analysis for C$_{14}$H$_{14}$N$_2$O$_2$.HCl: Calcd: C: 60.33, H: 5.42, N: 10.05, Found: C: 60.24, H: 5.45, N: 10.12.

EXAMPLE 29

1.3 g of ethyl 6-(1-imidazolylmethyl)-5,6,7,8-tetrahydro-2-naphthalenecarboxylate was mixed with 15 ml of a 5% solution of hydrogen chloride in ethanol, and the mixture was concentrated to dryness in vacuo. The residue was recrystallized from a mixture of isopropanol and diethyl ether to give 1.2 g of ethyl 6-(1-imidazolylmethyl)-5,6,7,8-tetrahydro-2-naphthalenecarboxylate hydrochloride as colorless crystals with m.p. 180°–182° C.

Analysis for C$_{17}$H$_{20}$N$_2$O$_2$.HCl: Calcd: C: 63.65, H: 6.60, N: 8.73, Found: C: 63.69, H: 6.51, N: 8.59.

While the invention has been described in detail and with reference to specific embodiments thereof, it will be apparent to one skilled in the art that various changes and modifications can be made therein without departing from the spirit and scope thereof.

What we claim is:

1. A compound of the formula (I)

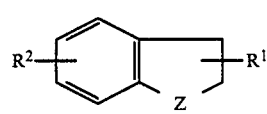

wherein:

Z represents methylene or ethylene, either one of R$^1$ and R$^2$ represents —(CH$_2$)$_m$—COOR$^3$ and the other represents,

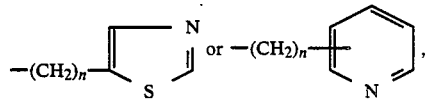

wherein R$^3$ represents a hydrogen atom or an alkyl group having 1 to 6 carbon atoms, n represents an integer of 1 to 6 and m represents an integer of 0 to 5, or a physiologically acceptable salt thereof.

2. A compound as claimed in claim 1, wherein R$^1$ represents

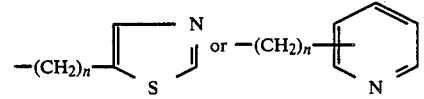

and R$^2$ represents —(CH$_2$)$_m$—COOR$^3$.

3. A compound as claimed in claim 1, wherein R$^1$ represents —(CH$_2$)$_m$—COOR$^3$ and R$^2$ represents

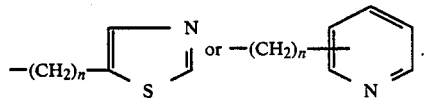

4. A compound as claimed in claim 1, wherein R$^1$ is

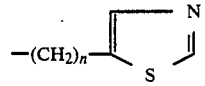

and R$^2$ is —(CH$_2$)$_m$—COOR$^3$.

5. A compound as claimed in claim 1, wherein R$^1$ is —(CH$_2$)$_m$—COOR$^3$ and R$^2$ is

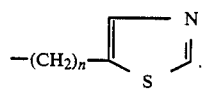

6. A compound as claimed in claim 1, wherein R¹ is

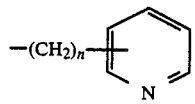

and R² is —(CH₂)$_m$—COOR³.

7. A compound as claimed in claim 1, wherein R¹ is —(CH₂)$_m$—COOR³ and R² is

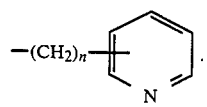

8. A compound as claimed in claim 1, wherein n is 1 or 2 and m is 0 or 1.

9. A compound as claimed in claim 4, wherein n is 1 or 2 and m is 0 or 1.

10. A compound as claimed in claim 6, wherein n is 1 or 2 and m is 0 or 1.

11. 6-(5-Thiazolylmethyl)-5,6,7,8-tetrahydro-2-naphthalenecarboxylic acid or a physiologically acceptable salt thereof according to claim 1.

12. 2-(5-Thiazolylmethyl)-5-indancarboxylic acid or a physiologically acceptable salt thereof according to claim 1.

13. 6-(3-Pyridylmethyl)-5,6,7,8-tetrahydro-2-naphthalenecarboxylic acid or a physiologically acceptable salt thereof according to claim 1.

14. 5-(2-(5-Thiazolyl)ethyl)-5,6,7,8-tetrahydro-1-naphthalenecarboxylic acid or a physiologically acceptable salt thereof according to claim 1.

* * * * *